（12）United States Patent
Sharp et al.

(10) Patent No.: US 12,419,868 B2
(45) Date of Patent: Sep. 23, 2025

(54) COMPOSITIONS AND METHODS FOR TREATING AND PREVENTING POST-CARDIOPULMONARY RESUSCITATION INJURY

(71) Applicant: THE UNIVERSITY OF CHICAGO, Chicago, IL (US)

(72) Inventors: Willard W Sharp, Chicago, IL (US); Lin Piao, Chicago, IL (US); Yonghu Fang, Chicago, IL (US)

(73) Assignee: The University of Chicago

( * ) Notice: Subject to any disclaimer, the term of this patent is extended or adjusted under 35 U.S.C. 154(b) by 200 days.

(21) Appl. No.: 17/025,022

(22) Filed: Sep. 18, 2020

(65) Prior Publication Data

US 2021/0085653 A1    Mar. 25, 2021

Related U.S. Application Data

(60) Provisional application No. 62/902,715, filed on Sep. 19, 2019.

(51) Int. Cl.
*A61K 31/426*    (2006.01)
*A61K 45/06*    (2006.01)
*A61P 11/00*    (2006.01)

(52) U.S. Cl.
CPC ............ *A61K 31/426* (2013.01); *A61K 45/06* (2013.01); *A61P 11/00* (2018.01)

(58) Field of Classification Search
None
See application file for complete search history.

(56) References Cited

PUBLICATIONS

Brand et al. "Suppressors of Superoxide-H2O2 Production at Site IQ of Mitochondrial Complex I Protect against Stem Cell Hyperplasia and Ischemia-Reperfusion Injury," Cell Metabolism 24, 582-592, Oct. 11, 2016. (Year: 2016).*
Madathil et al. "Ischemia reperfusion injury as a modifiable therapeutic target for cardioprotection or neuroprotection in patients undergoing cardiopulmonary resuscitation," Resuscitation 105 (2016) 85-91 (Year: 2016).*
Link et al. "Part 7: Adult Advanced Cardiovascular Life Support 2015 American Heart Association Guidelines Update for Cardiopulmonary Resuscitation and Emergency Cardiovascular Care," Circulation. 2015;132[suppl 2]:S444-S464 (Year: 2015).*
Khan M. "Pre-filled syringes emerging as one of the fastest-growing choices," LinkedIn Article. (Year: 2017).*
Chalkias et al. "Pathophysiology and pathogenesis of post-resuscitation myocardial stunning," Heart Fail Rev (2012) 17:117-128. (Year: 2012).*
Abel, E. D, "Mitochondrial dynamics and metabolic regulation in cardiac and skeletal muscle," Trans Am Clin Climatol Assoc 2018, 129:266-278.
Abella, B. S., et al., "Intra-arrest cooling improves outcomes in a murine cardiac arrest model," Circulation. 2004, 109 (22):2786-91.
Babini, G., et al., "Duration of Untreated Cardiac Arrest and Clinical Relevance of Animal Experiments: The Relationship Between the 'No Flow' Duration and the Severity of Post-Cardiac Arrest Syndrome in a Porcine Model," Shock 2018, 49(2):205-212.
Benjamin, E. J., et al., "Heart Disease and Stroke Statistics—2018 Update: A Report From the American Heart Association," Circulation 2018, 137(12) e67-e492.
Bolli, R., "Mechanism of myocardial 'stunning'," Circulation 1990, 82(3):723-738.
Brand, M. D., et al., "Suppressors of superoxide-H2O2 production at site IQ of mitochondrial complex I protect against stem cell hyperplasia and ischemia-reperfusion injury," Cell Metab 2016, 24(4):582-592.
Braunwald, E, et al., "The stunned myocardium: prolonged, postischemic ventricular dysfunction," Circulation 1982, 66(6):1146-1149.
Chang, W. T., et al, "Postresuscitation myocardial dysfunction: correlated factors and prognostic implications," Intensive Care Med 2007, 33(1):88-95.
Chouchani, E. T., et al., "Cardioprotection by S-nitrosation of a cysteine switch on mitochondrial complex I," Nat Med 2013, 19(6):753-759.
Chouchani, E. T., "Ischaemic accumulation of succinate controls reperfusion injury through mitochondrial ROS," Nature 2014, 515(7527):431-435.
Dezfulian, C., et al., "Mechanistic characterization of nitrite-mediated neuroprotection after experimental cardiac arrest," J Neurochem 2016, 139(3):419-431.
Dezfulian, C., et al., "Nitrite therapy after cardiac arrest reduces ROS generation, improves cardiac and neurological function, and enhances survival via reversible inhibition of mitochondrial complex I," Circulation 2009, 120(10):897-905.
Gorenkova, N. et al., "Conformational change of mitochondrial complex I increases ROS sensitivity during ischemia," Antioxid Redox Signal 2013, 19(13):1459-1468.
Hirschl, R. B, et al., "Severe myocardial dysfunction during extracorporeal membrane oxygenation," J Pediatr Surg 1992, 27(1):48-53.
Jentzer, J. C., et al., "Changes in left ventricular systolic and diastolic function on serial echocardiography after out-of-hospital cardiac arrest," Resuscitation 2018, 126:1-6.
Kern, K. B., et al., "Myocardial dysfunction after resuscitation from cardiac arrest: an example of global myocardial stunning," J Am Coll Cardiol 1996, 28(1):232-240.
Kleinman, M. E., et al., "Part 5: Adult Basic Life Support and Cardiopulmonary Resuscitation Quality: 2015 American Heart Association Guidelines Update for Cardiopulmonary Resuscitation and Emergency Cardiovascular Care," Circulation 2015, 132 (18 Suppl 2) p. S414-435.
Larsen, M. P., et al., "Predicting survival from out-of-hospital cardiac arrest: a graphic model," Ann Emerg Med 1993, 22(11)1652-1658.

(Continued)

*Primary Examiner* — Jeffrey S Lundgren
*Assistant Examiner* — Michael J Schmitt
(74) *Attorney, Agent, or Firm* — McDonnell Boehnen Hulbert & Berghoff LLP

(57) ABSTRACT

This disclosure relates generally to compositions and methods for treating and preventing post-cardiopulmonary resuscitation injury.

16 Claims, 12 Drawing Sheets

(56) References Cited

PUBLICATIONS

Laurent, I., et al., "Reversible myocardial dysfunction in survivors of out-of-hospital cardiac arrest," J Am Coll Cardiol 2002, 40(12):2110-2116.

MacFarlane, N. G., et al., "Depression of peak force without altering calcium sensitivity by the superoxide anion in chemically skinned cardiac muscle of rat," Circ Res 1992, 70(6):1217-1224.

Nolan, J. P., "Post-cardiac arrest syndrome: epidemiology, pathophysiology, treatment, and prognostication. A Scientific Statement from the International Liaison Committee on Resuscitation; the American Heart Association Emergency Cardiovascular Care Committee; the Council on Cardiovascular Surgery and Anesthesia; the Council on Cardiopulmonary, Perioperative, and Critical Care; the Council on Clinical Cardiology; the Council on Stroke," Resuscitation 2008, 79(3):350-379.

Paradies, G., et al., "Decrease in mitochondrial complex I activity in ischemic/reperfused rat heart: involvement of reactive oxygen species and cardiolipin," Circ Res 2004, 94(1):53-59.

Piao, L., et al., "FOXO1-mediated upregulation of pyruvate dehydrogenase kinase-4 (PDK4) decreases glucose oxidation and impairs right ventricular function in pulmonary hypertension: therapeutic benefits of dichloroacetate," J Mol Med (Berl) 2013, 91(3):333-346.

Roberts, B. W., et al., "Multiple organ dysfunction after return of spontaneous circulation in postcardiac arrest syndrome.,"Crit Care Med 2013, 41(6):1492-1501.

Sharp, W. W., et al., "Dynamin-related protein 1 (Drp1)-mediated diastolic dysfunction in myocardial ischemia-reperfusion injury: therapeutic benefits of Drp1 inhibition to reduce mitochondrial fission," FASEB J 2014, 28(1):316-326.

Sharp, W. W., et al., "Inhibition of the mitochondrial fission protein Drp1 improves survival in a murine cardiac arrest model," Crit Care Med 2015, 43(2):e38-47.

Song, M., et al., "Mitochondrial fission and fusion factors reciprocally orchestrate mitophagic culling in mouse hearts and cultured fibroblasts," Cell Metab 2015, 21(2):273-285.

Vanden Hoek, T. L., et al., "Reperfusion injury on cardiac myocytes after simulated ischemia," Am J Physiol 1996, 270 (4 Pt 2):H1334-1341.

Yang, L., et al., "Investigation of myocardial stunning after cardiopulmonary resuscitation in pigs," Biomed Environ Sci 2011, 24(2): 155-162.

Ytrehus, K., et al., "Rat and rabbit heart infarction: effects of anesthesia, perfusate, risk zone, and method of infarct sizing," Am J Physiol 1994, 267(6 Pt 2):H2383-2390.

Zhao, D., et al., "Intra-arrest cooling with delayed reperfusion yields higher survival than earlier normothermic resuscitation in a mouse model of cardiac arrest," Resuscitation 2008, 77(2):242-249.

American Heart Associate. "Heart Attack and Sudden Cardiac Arrest Differences". https://www.heart.org/en/health-topics/heart-attack/about-heart-attacks/heart-attack-or-sudden-cardiac-arrest-how-are-they-different#:~:text=A%20heart%20attack%20is%20when,is%20an%20%E2%80%9Celectrical%E2%80%9D%20problem (Accessed Nov. 8, 2003).

* cited by examiner

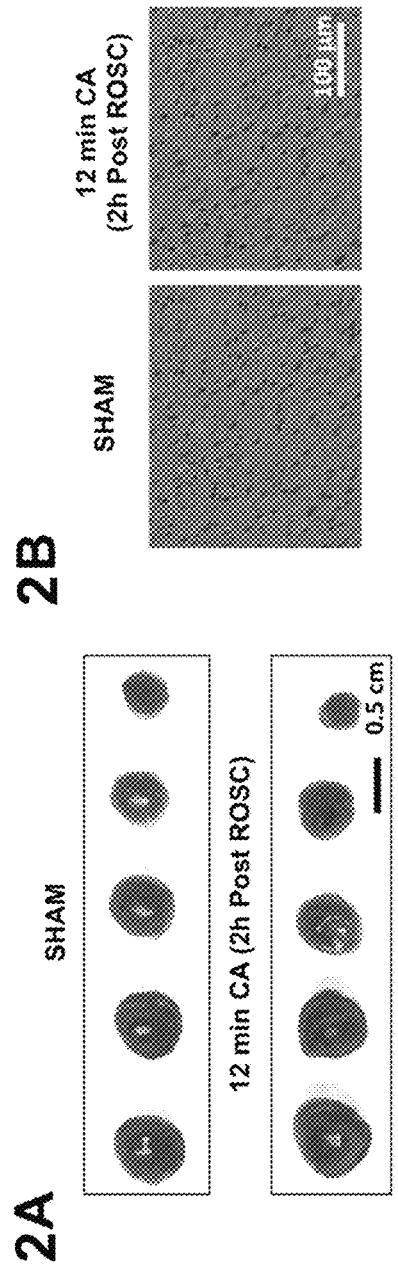
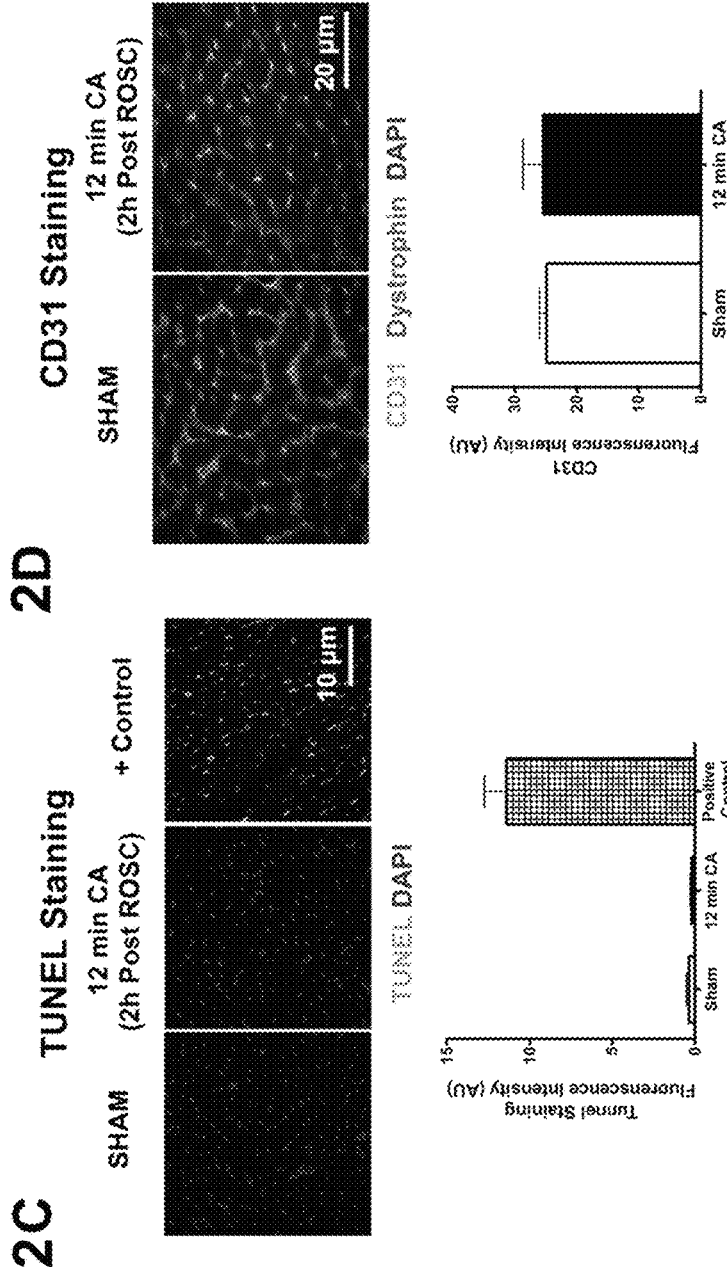
FIGS. 2A-2D

COMPOSITIONS AND METHODS FOR TREATING AND PREVENTING POST-CARDIOPULMONARY RESUSCITATION INJURY

CROSS-REFERENCE TO RELATED APPLICATIONS

This application claims priority to U.S. Provisional Application No. 62/902,715, filed Sep. 19, 2019, the disclosure of which is incorporated by reference herein.

STATEMENT REGARDING FEDERALLY SPONSORED RESEARCH OR DEVELOPMENT

This invention was made with government support under RO1HL133675 awarded by the National Institutes of Health. The government has certain rights in the invention.

BACKGROUND OF THE DISCLOSURE

Field of Disclosure

This disclosure relates generally to compositions and methods for treating and preventing post-cardiopulmonary resuscitation injury.

Technical Background

Sudden cardiac arrest (CA) both in and out of hospital is common and has high morbidity and mortality (1). Early, high-quality, cardiopulmonary resuscitation (CPR) has been demonstrated to increase survival, but its effectiveness deteriorates within minutes if its initiation is delayed (2, 3). Delayed CPR is common and often associated with cardiogenic shock resulting in hemodynamic instability and poor neurological outcomes (4). The severity of post-CPR shock may also contribute to the extent of neurological outcomes in surviving patients (5). Post-CPR cardiogenic shock occurs even in the absence of acute coronary artery occlusion and is a component of the "post-CA syndrome" (5, 6). The pathophysiology of post-CPR cardiogenic shock is unknown and effective therapies are lacking.

Myocardial ischemia of short duration followed by adequate coronary flow restoration results in reversible myocardial dysfunction without necrosis. This cardiac pathology is termed myocardial stunning (7, 8). It was originally used to describe regional non-infarcted ventricular wall movement abnormalities, following brief coronary artery occlusion/reperfusion injuries, but has since been used to describe patients experiencing cardiogenic shock after percutaneous coronary artery intervention and cardiopulmonary bypass surgery (9, 10). Myocardial stunning is not commonly recognized as mediating post-CPR shock and although it has been described in the setting of ventricular fibrillation induced CA (8, 11), it has not been studied in other forms of CA, such as asystolic CA. Furthermore, the molecular mechanisms mediating myocardial stunning are unknown since it has been described as "lacking clinical relevance" (9).

Myocardial mitochondria occupy ⅓ of the heart's volume and are central regulators of calcium, reactive oxygen species (ROS), and metabolism. Mitochondria are dynamic organelles undergoing regulated fusion (joining) and fission (dividing) events (12, 13). This group was the first to demonstrate evidence of mitochondrial fission following CA, its mediation of myocardial dysfunction through fission-induced ROS generation (14). In addition to mitochondrial fission, the accumulation of succinate during cellular ischemia results in increased electron leak and generation of superoxide and/or $H_2O_2$ (15, 16). Limiting electron leak and ROS generation using inhibitors of mitochondrial electron transport during IR have shown promise, but their utility is limited by their negative effects on metabolism (17-19).

Recently, compounds have been identified that protect against $H_2O_2$ production induced by electron leak at sites $I_Q$ (the ubiquinone-binding site of complex I, the active site during reverse electron transport), $II_F$ (the flavin site of complex II), or $III_{Qo}$ (the outer ubiquinone-binding site of complex III) in isolated skeletal muscle (16). However, the utility of such compounds for treating and preventing post-resuscitation injury has not been established. Therefore, there remains a need to identify new therapies that are effective for improving post-resuscitation health.

SUMMARY OF THE DISCLOSURE

Provided herein are compositions, methods, and devices for treating and preventing post-cardiopulmonary resuscitation injury.

In a first aspect, the present disclosure provides a method of treating or preventing post-cardiopulmonary resuscitation (CPR) injury in a subject, comprising administering a pharmaceutical composition to the subject, the pharmaceutical composition comprising a therapeutically effective amount of a compound that reduces or inhibits $H_2O_2$ production induced by electron leak at sites $I_Q$ (the ubiquinone-binding site of Complex I, the active site during reverse electron transport), $II_F$ (the flavin site of Complex II), or $III_{Qo}$ (the outer ubiquinone-binding site of Complex III).

In one embodiment of the first aspect, the pharmaceutical composition improves post-CPR mitochondrial function in the subject.

In one embodiment of the first aspect, the pharmaceutical composition reduces post-CPR cardiac mitochondrial ROS generation in the subject.

In one embodiment of the first aspect, the pharmaceutical composition increases the rate of post-CPR return to spontaneous circulation in the subject.

In one embodiment of the first aspect, the pharmaceutical composition increases post-CPR myocardial contractility in the subject.

In one embodiment of the first aspect, the pharmaceutical composition improves post-CPR neurological function in the subject.

In one embodiment of the first aspect, the pharmaceutical composition reduces post-CPR neurological injury in the subject.

In one embodiment of the first aspect, the pharmaceutical composition improves survival rate in the subject.

In one embodiment of the first aspect, the compound comprises suppressor of site IQ electron leak (S1QEL).

In one embodiment of the first aspect, the pharmaceutical composition is administered to the subject prior to, at the same time as, and/or after administration of cardiopulmonary resuscitation to the subject.

In one embodiment of the first aspect or embodiments thereof, the pharmaceutical composition further comprises one or more secondary therapeutic agents. In one embodiment, the one or more secondary therapeutic agents is selected from adrenaline (epinephrine), atropine, amiodarone, adenosine, calcium chloride, chlorphenamine, furosemide, glucose, hydrocortisone, lidocaine, magnesium sulfate, midazolam, naloxone, sodium chloride, potassium chloride, and sodium bicarbonate, and mixtures thereof.

In one embodiment of the first aspect, the method further comprises administering a therapeutically effective amount of a secondary therapeutic agent to the subject prior to, at the same time as, and/or after administration of the pharmaceutical composition to the subject. In one embodiment, the one or more secondary therapeutic agents is selected from adrenaline (epinephrine), atropine, amiodarone, adenosine, calcium chloride, chlorphenamine, furosemide, glucose, hydrocortisone, lidocaine, magnesium sulfate, midazolam, naloxone, sodium chloride, potassium chloride, and sodium bicarbonate, and mixtures thereof.

In a second aspect, the present disclosure provides a device for treating a subject in need of CPR including a therapeutically effective amount of a compound that reduces or inhibits $H_2O_2$ production induced by electron leak at sites $I_Q$ (the ubiquinone-binding site of complex I, the active site during reverse electron transport), $II_F$ (the flavin site of complex II), or $III_{Qo}$ (the outer ubiquinone-binding site of complex III).

In one embodiment of the second aspect, the device comprises a prefilled syringe, an ampoule, an autoinjector, a nasal insufflator, a metered-dose inhaler, a dry-powder inhaler, a vaporizer, a nebulizer, a pump sprayer, an aerosol can, a softgel, or a dermal patch.

In a third aspect, the present disclosure provides a pharmaceutical composition, including a therapeutically effective amount of a compound that reduces or inhibits $H_2O_2$ production induced by electron leak at sites $I_Q$ (the ubiquinone-binding site of complex I, the active site during reverse electron transport), $II_F$ (the flavin site of complex II), or $III_{Qo}$ (the outer ubiquinone-binding site of complex III) and a pharmaceutically acceptable carrier, solvent, adjuvant, diluent, or a combination thereof.

In one embodiment of the third aspect, the pharmaceutical composition further includes one or more secondary therapeutic agents. In one embodiment, the one or more secondary therapeutic agents is selected from adrenaline (epinephrine), atropine, amiodarone, adenosine, calcium chloride, chlorphenamine, furosemide, glucose, hydrocortisone, lidocaine, magnesium sulfate, midazolam, naloxone, sodium chloride, potassium chloride, and sodium bicarbonate, and mixtures thereof.

In one embodiment of the third aspect, the compound comprises S1QEL.

In a fourth aspect, the present disclosure provides a method of treating or preventing brain injury or neurological disease in a subject resulting from mitochondrial complex 1 injury or disease. The method includes administering a pharmaceutical composition to the subject, wherein the pharmaceutical composition includes a therapeutically effective amount of a compound that reduces or inhibits $H_2O_2$ production induced by electron leak at sites $I_Q$ (the ubiquinone-binding site of Complex I, the active site during reverse electron transport), $II_F$ (the flavin site of Complex II), or $III_{Qo}$ (the outer ubiquinone-binding site of Complex III).

In one embodiment of the first aspect, the neurological disease includes Parkinson's disease or Leigh Syndrome.

Other aspects, features, and advantages of the present disclosure will become apparent from the following detailed description. It should be understood, however, that the detailed description and the specific examples, while indicating specific embodiments of the disclosure, are presented as illustrations only, since various changes and modifications within the spirit and scope of the invention will become apparent to those skilled in the art.

BRIEF DESCRIPTION OF THE DRAWINGS

The accompanying drawings are included to provide a further understanding of the methods and materials of the disclosure, and are incorporated in and constitute a part of this specification. The drawings illustrate one or more embodiment(s) of the disclosure and, together with the description, serve to explain the principles and operation of the disclosure.

FIGS. 2A-2D: Post-CPR myocardial dysfunction occurs in the absence of myocardium necrosis. 2(A) Tetrazolium staining of hearts 2 hours following a 12 min CA. H&E staining 2(B), TUNEL staining 2(C) and CD31 staining 2(D) of left ventricle sections 2 hours following CA compared to Sham.

Survival curve following CA with S1QEL and controls. S, S1QEL; n=53, 39, respectively. *, P<0.05; , P<0.01; *, P<0.001 vs CA group.

Figure 6:
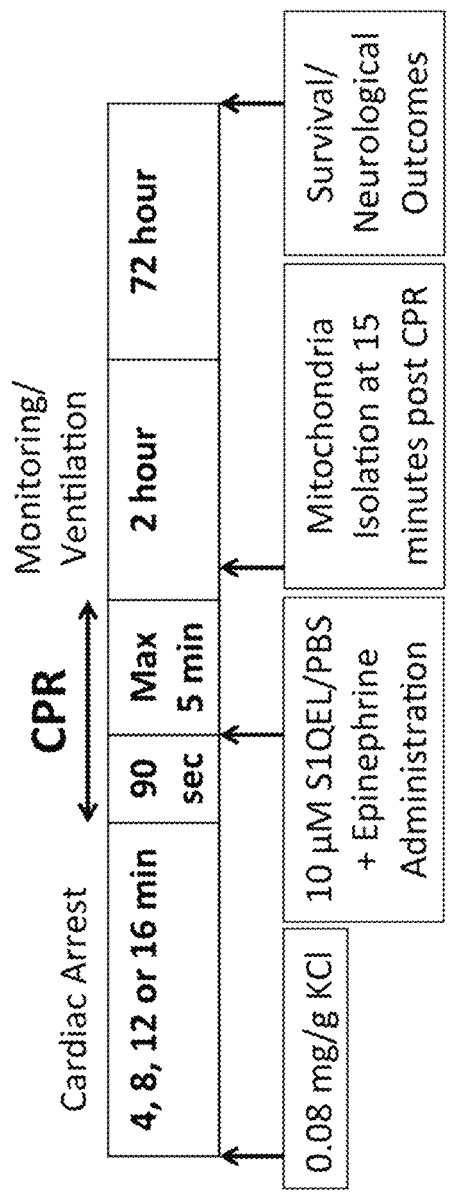

FIG. 6: Schematic of Experimental Protocol. 6-8 month-old female C57B6 were subjected to an asystolic, non-ventilated cardiac arrest induced by KCl. Ventilations and chest compressions were then performed for 90 seconds followed by intravenous epinephrine with or without S1QEL or PBS administration. CPR was then continued until ROSC or terminated after 5 minutes. Mice achieving ROSC were monitored and ventilated for 2 hours. Survival and Neurological outcomes were then monitored at 72 hours.

Figure 7:
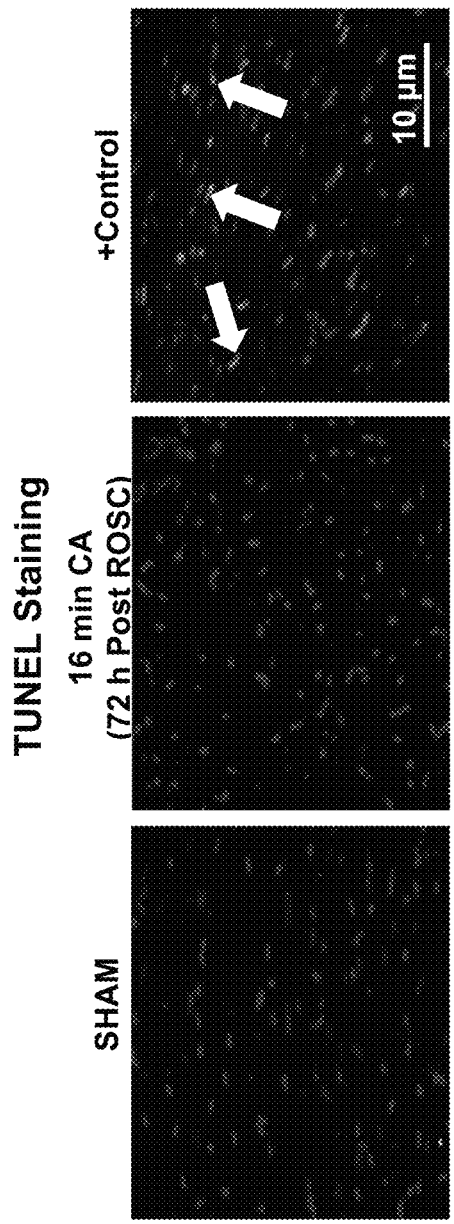

FIG. 7: Post-CPR myocardial dysfunction occurs in absent of myocardium apoptosis. TUNEL staining (arrows) of left ventricle at 72 hours following a 16 min CA compared to Sham and positive control.

Figure 8:
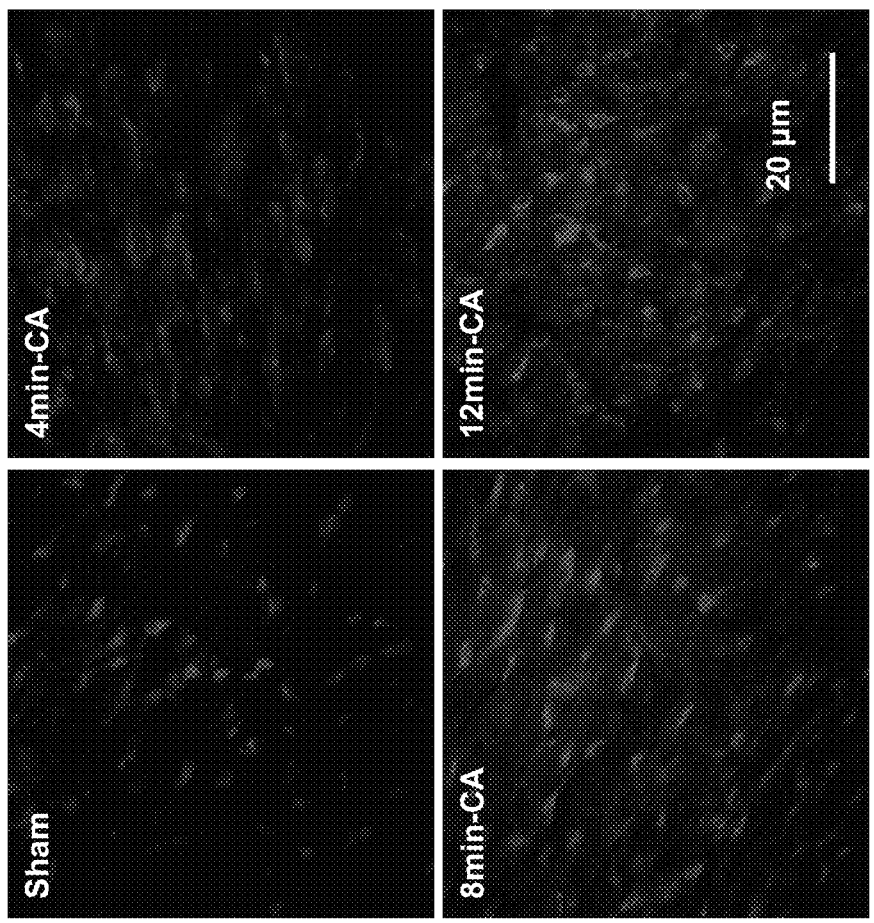

FIG. 8: Post-CPR ROS production increases as CA duration is prolonged. MitoSox staining of left ventricle tissue sections from 4-minute, 8-minute, 12-minute CA, and Sham mice.

FIGS. 9A-9D: Post-CPR mitochondrial complex II injury. Mitochondrial complex II OCR is measured using the complex I inhibitor rotenone and the substrate succinate. The sequential injection of mitochondrial inhibitors is indicated by arrows 9(A). Bar graphs show ADP induced OCR 9(B), State 3/State 4 9(C), maximal OCR following FCCP 9(D) and proton leak 9(E). n=7, respectively. *, P<0.05; , P<0.01; *, P<0.001 vs Sham.

Figures 10A, 10B, 10C:
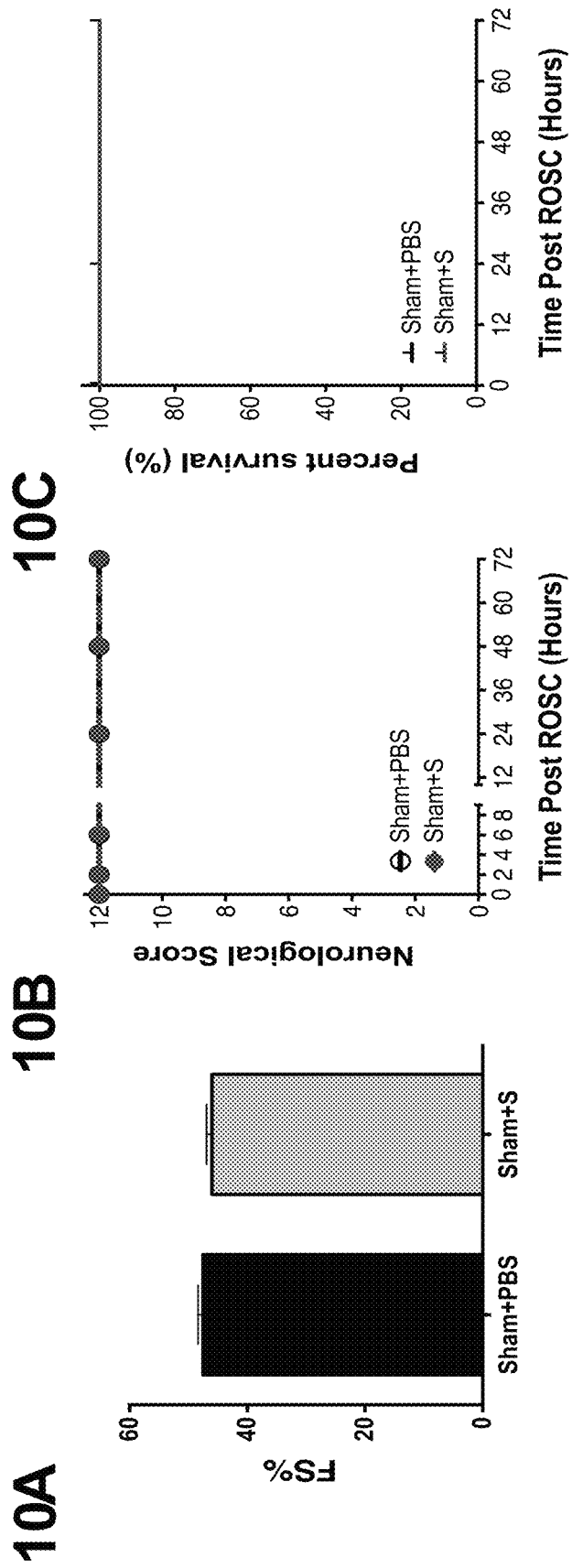

FIG. 10: S1QEL alone doesn't alter cardiac function, neurological function and survival. S1QEL (10 μM) has no effect on FS % 10(A), neurological score 10(B) and survival 10(C). n=6 in each group. P>0.05 vs Sham.

Figures 11A, 11B:
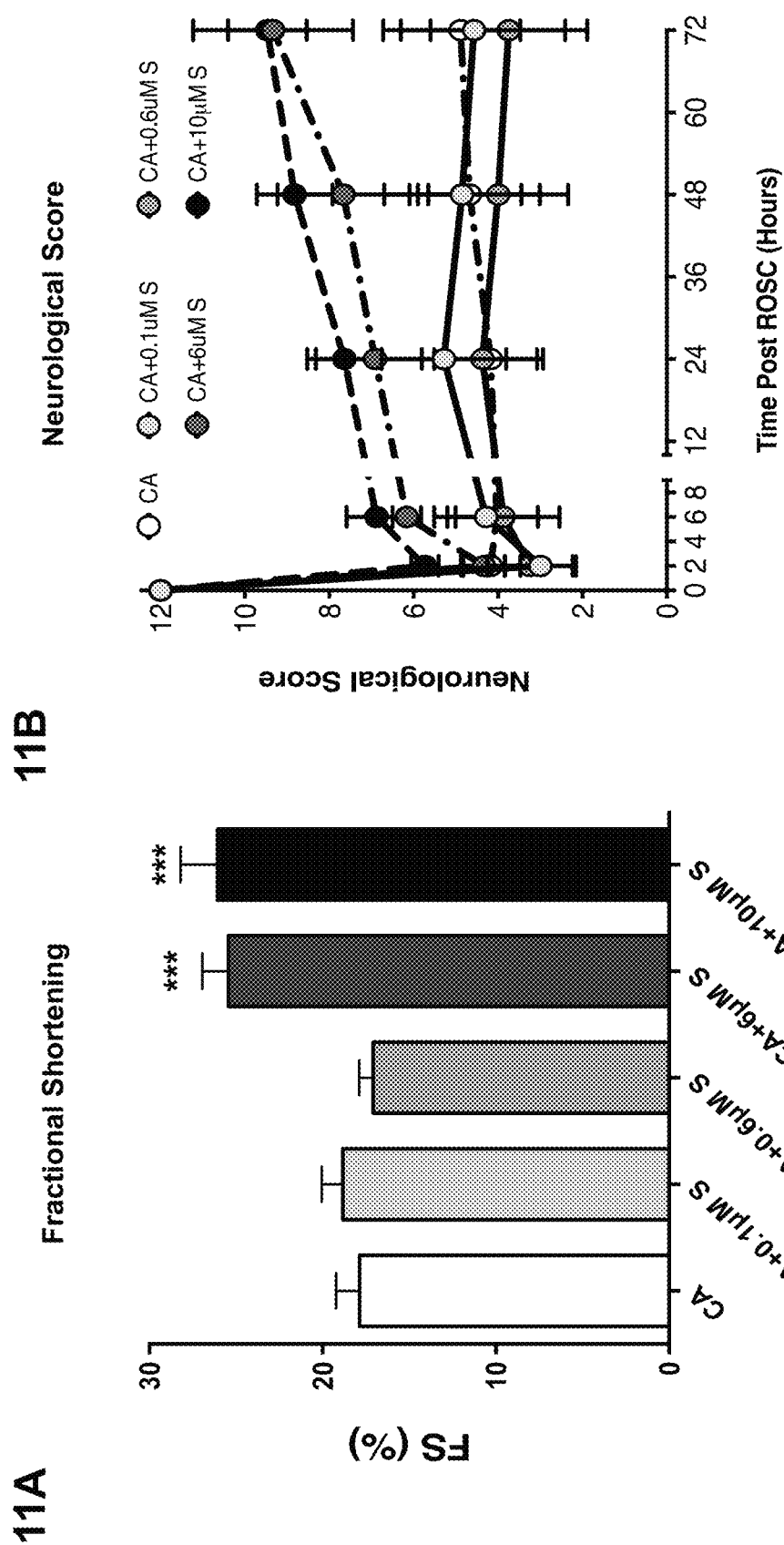
Figures 12A, 12B, 12C, 12D:
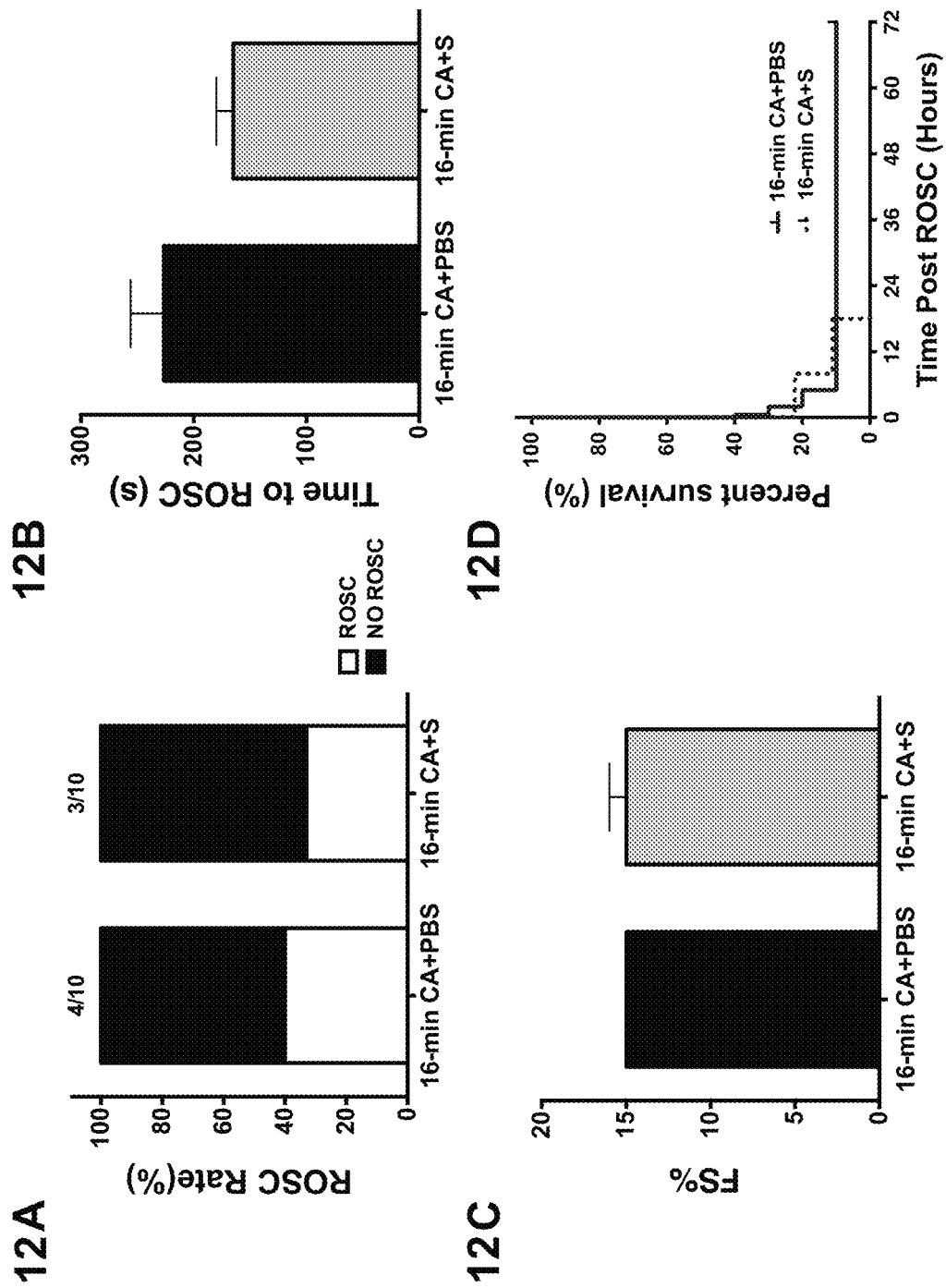

FIGS. 11A-11B: S1QEL improves cardiac and neurological functions post CPR resuscitation. 11(A) Left ventricular fractional shortening following 12 min cardiac arrest with S1QEL (0.1 μM, 0.6 μM, 6 μM and 10 μM) and controls. 11(B) Neurological scores in mice following cardiac arrest with S1QEL and controls. n=6, 6, 8, 8 and 10, respectively. ***, P<0.001 vs cardiac arrest group.

FIGS. 12A-12D: S1QEL has no effect on ROSC rate 12(A), time to ROSC 12(B), FS % 12(C) and neurological function 12(D) post 16-min cardiac arrest. n=10 in each group. P>0.05 vs 16-min cardiac arrest group.

DETAILED DESCRIPTION

Before the disclosed methods and materials are described, it is to be understood that the aspects described herein are not limited to specific embodiments, and as such can, of course, vary. The compositions and methods described herein can be configured by the person of ordinary skill in the art to meet the desired need. It is also to be understood that the terminology used herein is for the purpose of describing particular aspects only and, unless specifically defined herein, is not intended to be limiting.

The present disclosure establishes the utility of suppressor of site IQ electron leak (S1QEL) as a therapeutic agent for improving patient health post-resuscitation from cardiac arrest.

Therapeutic Methods

The present disclosure provides methods of treating post-resuscitation injury in a subject in need thereof. A subject needing treatment in the present context can be an individual (for example, a human or other mammal) who has suffered, is suffering, or will suffer cardiac arrest (CA). In some embodiments, the subject can have suffered or will suffer a heart attack. Contemplated methods include administering to the subject a therapeutically effective amount of a pharmaceutical composition as described herein.

In certain embodiments of the disclosure, the therapeutically effective amount of the pharmaceutical composition is an amount sufficient to treat or inhibit cardiogenic shock or myocardial stunning in a subject in need thereof. In some embodiments, the therapeutically effective amount of the pharmaceutical composition (or a therapeutically effective amount of a therapeutic agent contained therein) is an amount that improves post-CPR mitochondrial function, reduces post-CPR cardiac mitochondrial ROS generation, increases the rate of post-CPR return to spontaneous circulation, increases post-CPR myocardial contractility, improves post-CPR neurological function, reduces post-CPR neurological injury, and/or improves survival rate in the subject.

The present inventors have advantageously determined that the pharmaceutical compositions of the disclosure are particularly suitable for treating and preventing post-resuscitation injury. More particularly, administration of a therapeutically effective amount of a compound that reduces or inhibits $H_2O_2$ production induced by electron leak at sites $I_Q$ (the ubiquinone-binding site of Complex I, the active site during reverse electron transport), $II_F$ (the flavin site of Complex II), or $III_{Qo}$ (the outer ubiquinone-binding site of Complex III) is effective for treating and preventing post-CPR injury. Unexpectedly, the methods and compositions disclosed also improved post-CPR neurological function and/or reduced post-CPR neurological injury post-CA. These beneficial effects on neurological function may be secondary to improved cardiac function and/or they may be a direct effect on central and/or peripheral neural tissues post-CA.

The methods disclosed herein can be particularly useful when performed by first responders, such as fire fighters, police, EMS providers, and other health care professionals when preparing to begin, beginning, or continuing to provide cardiopulmonary resuscitation on a cardiac arrest victim. Without wishing to be bound by theory, it is believed that the methods disclosed herein improve the chances (e.g., increase the likelihood) of a subject surviving cardiac arrest and also surviving cardiac arrest with fewer deleterious effects caused by the cardiac arrest.

In some embodiments, methods contemplated herein include administering to a subject in need thereof an effective amount of a pharmaceutical composition that includes a compound that reduces or inhibits $H_2O_2$ production induced by electron leak at sites $I_Q$ (the ubiquinone-binding site of complex I, the active site during reverse electron transport), $II_F$ (the flavin site of complex II), or $III_{Qo}$ (the outer ubiquinone-binding site of complex III).

In one embodiment, the method treats or prevents brain injury or neurological disease in a subject resulting from mitochondrial complex 1 injury or disease.

In some embodiments, the neurological disease includes Parkinson's disease or Leigh Syndrome.

Compositions

The present disclosure is also directed to pharmaceutical compositions that include a compound that reduces or inhibits $H_2O_2$ production induced by electron leak at sites $I_Q$ (the ubiquinone-binding site of complex I, the active site during reverse electron transport), $II_F$ (the flavin site of complex II), or $III_{Qo}$ (the outer ubiquinone-binding site of complex III). In one embodiment, the compound is S1QEL or a derivative thereof. Such compositions may further include an appropriate pharmaceutically acceptable carrier, solvent, adjuvant, diluent, or any combination thereof. The exact nature of the carrier, solvent, adjuvant, or diluent will depend upon the desired use (e.g., route of administration) for the composition, and may range from being suitable or acceptable for veterinary uses to being suitable or acceptable for human use.

The pharmaceutical compositions as described herein may be administered singly, as mixtures of one or more compounds, or in mixture or combination with other (secondary) therapeutic agents useful for treating cardiac arrest and associated symptoms or diseases.

Non-limiting examples of contemplated secondary therapeutic agents that can be used herein include adrenaline (epinephrine), atropine, amiodarone, adenosine, calcium chloride, chlorphenamine, furosemide, glucose, hydrocortisone, lidocaine, magnesium sulfate, midazolam, naloxone, sodium chloride, potassium chloride, and sodium bicarbonate, and mixtures thereof.

Pharmaceutical compositions may take a form suitable for virtually any mode of administration, including, for example, injection, transdermal, oral, topical, ocular, buccal, systemic, nasal, rectal, vaginal, etc., or a form suitable for administration by inhalation or insufflation.

The compound(s) described herein, or compositions thereof, will generally be used in an amount effective to achieve the intended result, for example in an amount effective to treat or prevent the particular condition being treated. By therapeutic benefit is meant eradication or amelioration of the underlying disorder (e.g., myocardial dysfunction) being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the condition (e.g., associated injury and/or symptoms stemming from cardiac arrest).

The amount of compound(s) administered will depend upon a variety of factors, including, for example, the particular indication being treated (e.g., the degree or severity of cardiac arrest or cardiac dysfunction), the mode of administration, whether the desired benefit is prophylactic (e.g., when a subject is at risk for experiencing cardiac arrest due to underlying disease, injury, surgical procedure, or heart transplant) or therapeutic (e.g., when a subject has experienced cardiac arrest due to underlying disease, injury, surgical procedure, or heart transplant), and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an IC50 of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts can be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, including particular condition being treated, the severity of existing or anticipated cardiac dysfunction, the genetic profile, age, health, sex, diet, and/or weight of the subject. Dosage amount and interval may be adjusted individually to provide plasma levels of the compound(s) and/or active metabolite of the compound(s) which are sufficient to maintain therapeutic or prophylactic effect. For example, the compounds may be administered once, or once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

For example, a dosage contemplated herein can include a single volume of about 0.1, 0.2, 0.3, 0.4, 0.5, 0.6, 0.7, 0.8, 0.9, 1.0, 1.5, 2.0, 2.5, or 3.0 mL of a composition having a concentration of S1QEL at about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 10, 15, 20, 50, 100, 200, 500, or 1000 µM in a pharmaceutically acceptable carrier.

Devices

Further contemplated herein are devices containing one or more pharmaceutical compositions described herein that can be used to administer the one or more pharmaceutical compositions to an individual in need thereof. Contemplated devices can take any form that is appropriate for the intended route of administration of the pharmaceutical compound. For example, contemplated devices include prefilled syringes, ampoules, autoinjectors, nasal insufflator, a metered-dose inhaler, a dry-powder inhaler, a vaporizer, a nebulizer, a pump sprayer, an aerosol can, a softgel (or other fast release oral dosage form), a dermal patch, and other devices capable of carrying and/or delivering a therapeutically effective amount of a pharmaceutical composition contemplated herein.

In one embodiment, a device according to the present disclosure can be carried by an individual, such as a first responder, emergency medical technician, doctor, nurse, or caregiver in anticipation of needing to treat a subject who will experience cardiac arrest. Should the subject experience cardiac arrest, the individual (who may be the subject) can administer the pharmaceutical composition within the device, such as an autoinjector, to the subject prior to, during, or after administration of CPR.

Definitions

The following terms and expressions used herein have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an," and "the" include plural referents unless the context clearly dictates otherwise.

Similarly, when values are expressed as approximations, by use of the antecedent "about," it will be understood that the particular value forms one possible embodiment and variation of the given value is possible (e.g., about 80 may include 80±10%). It will be further understood that the endpoints of each of the ranges are significant both in relation to the other endpoint, and independently of the other endpoint.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z."

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Therapeutically effective amount" or "effective amount" refers to that amount of a compound which, when administered to a subject, is sufficient to effect treatment for a condition or disorder described herein. The amount of a compound which constitutes a "therapeutically effective amount" or "effective amount" will vary depending on the compound, the condition or disorder and its severity, and the age of the subject to be treated, but can be determined routinely by one of ordinary skill in the art.

"Treating" or "treatment" as used herein covers the treatment of a condition or disorder described herein, in a subject, preferably a human, and includes:
 i. inhibiting a condition or disorder, i.e., arresting its development (e.g., mitochondrial ROS production associated with cardiac arrest);
 ii. relieving a condition or disorder, i.e., causing regression of the disorder (e.g., restoring normal cardiac function);
 iii. slowing progression of the disorder; and/or
 iv. inhibiting, relieving, ameliorating, or slowing progression of one or more symptoms of the condition or disorder.

"Subject" refers to a warm blooded animal such as a mammal, preferably a human, which is afflicted with, or has the potential to be afflicted with one or more conditions and disorders described herein.

EXAMPLES

Certain aspects of the disclosure are illustrated further by the following examples, which are not to be construed as limiting the disclosure in scope or spirit to the specific methods and materials described in them.

Example 1: S1QEL Improves Myocardial Function, Neurological Outcomes, and Survival Following Cardiopulmonary Resuscitation Overview Background—Cardiogenic shock following cardiopulmonary resuscitation (CPR) for sudden cardiac arrest is common, occurring even in the absence of acute coronary artery occlusion, and contributes to high rates of post-CPR mortality. The pathophysiology of this shock is unclear and effective therapies for improving clinical outcomes are lacking.

Methods and Results—Using a murine model of asystolic cardiac arrest, the pathophysiology of post-CPR cardiogenic shock was investigated and it was discovered that duration of cardiac arrest (4, 8, 12, or 16 minutes) prior to CPR determined post-resuscitation success rates, degree of neurological injury, and severity of myocardial dysfunction. Post-CPR cardiac dysfunction was not associated with myocardial necrosis, apoptosis, inflammation, or mitochondrial permeability transition pore opening and recovered within several days, indicative of myocardial stunning. Post-CPR myocardial stunning was associated with increases in ventricular and mitochondrial reactive oxygen species (ROS, $P<0.001$ vs Sham, respectively). Seahorse micropolarimetry of isolated post-CPR cardiac mitochondria revealed decreased rates of maximal oxygen consumption rates (OCR) for both Complex I and Complex II vs controls ($P<0.01$ vs Sham, respectively), indicating inhibition of mitochondrial oxidative phosphorylation. Paradoxically, in the presence of ADP stimulated coupled respiration, post-CPR mitochondria demonstrated increased OCR ($P<0.05$ vs Sham) and increased rates of proton leak ($P<0.05$ vs Sham), suggesting Complex I as the site of ROS generation. These findings were not observed at complex II. Suppressor of site IQ electron leak (S1QEL), a complex I-specific superoxide inhibitor, administered during CPR, decreased myocardial ROS generation while improving post-CPR myocardial function ($P<0.01$ vs CPR control), neurological injury ($P<0.01$ vs CPR control), and survival ($P<0.01$ vs CPR control).

Conclusions—The results demonstrate that cardiogenic shock following resuscitation from cardiac arrest is consistent with myocardial stunning mediated by mitochondrial complex I injury and ROS generation. Targeting this mechanism represents a novel and practical therapy for improving sudden cardiac arrest resuscitation outcomes. S1QEL has been reported as reducing reactive oxygen species and has been reported as a possible therapy for myocardial infarction through in vitro testing but had never been tested in vivo. Furthermore, it was unknown if it could help survival following sudden cardiac arrest by improving cardiopulmonary resuscitation (CPR) outcomes.

This work improves on prior work in three major aspects: 1) this work for the first time demonstrates S1QEL is effective in a living animal following cardiac arrest; 2) prior work only theorized that S1QEL would improve outcomes for heart attacks. However, cardiac arrest is often caused by arrhythmias unrelated to heart attacks so it was unclear if it would have any efficacy at improving cardiopulmonary resuscitation outcomes; and 3) this work demonstrates that S1QEL improves neurological outcomes in an animal model which has not been previously demonstrated. Prior work has only shown improvement in cellular in vitro systems and in perfused heart systems.

Introduction

Recently, Brand et al. identified compounds that protect against $H_2O_2$ production induced by electron leak at sites $I_Q$ (the ubiquinone-binding site of complex I, the active site during reverse electron transport), $II_F$ (the flavin site of complex II), or $III_{Qo}$ (the outer ubiquinone-binding site of complex III) in isolated skeletal muscle (16). One compound, S1QEL (the suppressor of site IQ electron leak), limited ROS generation at complex I without affecting normal electron transport. S1QEL also attenuated oxidative damage in several cell types while limiting infarct size in Langendorff perfused mouse hearts. In this study, it was hypothesized that the severity of cardiogenic shock following CPR is dependent on the length of cardiac arrest (CA) and by virtue of lacking myocardial necrosis, is reversible, consistent with myocardial stunning. Furthermore, it was hypothesized that myocardial stunning is mediated by increased mitochondrial complex I ROS generation and that its therapeutic targeting by S1QEL could improve post-resuscitation outcomes. Findings in this study support the hypothesis and suggest that S1QEL has potential as a therapeutic agent to improve outcomes in CA.

Material and Methods

Cardiac Arrest Mice Model

Adult (age 6-8 months, 20-30 g) retired breeder female C57BL/6 mice were anesthetized with 3% vaporized isoflurane and intubated/ventilated as previously described (29). This work was based on the original work of Abella et al. (30), which used retired female breeders. Cardiac arrest typically affects older adults so this study, similar to previous studies, used older mice to reflect this population. These previous studies, similar to this study, used female mice because female aged mice are easier to obtain than male mice from animal supplier since they are kept for longer periods of time for breeding purposes. Because there are no observed differences between men and women regarding outcomes following sudden cardiac death, this approach has been used by cardiac arrest researchers utilizing aged mice. Asystolic CA was induced by an intravenous bolus of 0.08 mg/g KCl via a jugular vein catheter, and the ventilator was disconnected. Following 4, 8, 12, or 16 minutes of CA, the ventilator was reconnected and manual chest compressions were performed at a rate 350~400 bpm. After 90 seconds of cardiopulmonary resuscitation (CPR), 1.5 µg of epinephrine was injected. CPR was terminated when return of spontaneous circulation rates (ROSC) was achieved (defined by a sinus rhythm with a mean arterial pressure greater than 40 mmHg lasting at least 5 minutes) or after 5 minutes of unsuccessful CPR. Resuscitated animals received intravenous 0.9% saline at a rate of 100 µL/h and were monitored on mechanical ventilation for up to 120 minutes. Animals for survival studies or neurological function studies were returned to the animal facility and observed for 72 hours post CA. All the chemicals were purchased from Sigma (St Louis, MO). Suppressor of site $I_Q$ electron leak (51QEL), is able to reduce superoxide-$H_2O_2$ production from site $I_Q$ by 40-85% at a dose of 10 µM (31). S1QEL or PBS was given to mice along with the injection of epinephrine in a blinded fashion after 90 seconds of CPR. An illustration of the CA protocol used this study was provided in FIG. 6.

In accordance with National Institutes of Health guidelines, the University of Chicago IACUC approved of all animal procedures. A total of 121 mice entered the study. Among them, 22 mice died due to surgical failure; 49 mice could not be resuscitated. Additional details are described elsewhere herein.

Neurological Scoring of Animals

Neurological deficits after cardiac arrest (2 h, 6 h, 24 h, 48 h, and 72 h) in mice were determined using a 12-point mouse neurological scoring system (20). Scores ranged from 0 (no response or worst) to 2 (normal) along 6 domains: paw pinch, righting reflex, breathing, spontaneous movement, motorglobal, and motor-focal. The scores for each of the 6 domains were determined in a blinded fashion and summed to achieve the neurological score.

Mitochondria Isolation

Mitochondria were obtained from post-CA hearts as previously described (13). Briefly, hearts from Sham and post-CA mice were collected at 15 minutes after CPR, then minced and incubated with trypsin before homogenization with a glass/Teflon Potter Elvehjem homogenizer (Fisher Scientific, Hanover Park, IL, USA). Heart homogenates were centrifuged at 800 g×5 min at 4° C. and the supernatant collected and centrifuged at 8,000 g×5 min at 4° C. twice to obtain purified cardiac mitochondria.

Mitochondrial Permeability Transition Pore Opening

Mitochondrial permeability transition pore (mPTP) opening induced by calcium was determined in freshly isolated cardiac mitochondria (13). Cardiac mitochondria (250 µg/mL) were suspended in 200 µL reaction buffer containing 120 mM KCl, 10 mM Tris (pH 7.6), and 5 mM $KH_2PO_4$ and stimulated by the addition of 1 mM $CaCl_2$. The absorbance was continuously measured using a Cytation 3 (BioTek, Winooski, VT, USA) 96 well plate reader at 540 nm (35).

Complex I Enzyme Activity

Complex I activity was measured using an enzyme activity dipstick assay (Abcam, Cambridge, MA) following the manufacturer's protocol. In principle, immunocaptured Complex I oxidizes NADH, and the resulting H+ reduces nitrotetrazolium blue (NBT) to form a blue-purple precipitate at the complex I antibody line on the dipstick immersed in complex I activity buffer containing NADH (substrate) and NBT (electron acceptor). The signal intensity of this precipitate corresponds to the level of complex I enzyme activity (blue band) in the sample. The intensity was analyzed by using Fiji 6 (NIH, public domain).

Superoxide $H_2O_2$ Production in Cardiac Mitochondria

To induce $H_2O_2$ production from site $I_Q$ in cardiac mitochondria, 20 mM glycerol 3-phosphate was added to isolated mitochondria (1 µg/100 µL) in respiration medium with 50 µM Amplex Red and 2 mU/mL horseradish peroxidase (16). Fluorescence was monitored using a microplate reader (SpectraMax iD3, Molecular Devices, Sunnyvale, CA) for excitation at 540 nm and emission detection at 590 nm at 37° C. after 30 minutes incubation.

Seahorse Measurement of Mitochondrial Oxygen Consumption Rates

Isolated mitochondria (1 µg/100 µL) from the hearts of Sham and post-CPR mice were suspended in 24-well plates. Oxygen consumption rates (OCR) were determined using the Seahorse XF24 Extracellular Flux Analyzer (Seahorse Bioscience, Billerica, MA), as previously described (21). Complex I OCR was measured using the substrates 10 mM pyruvate+2 mM malate. Complex II OCR was measured using the substrate 10 mM succinate and an inhibitor of reverse electron flow, 2 µM rotenone.

The measurement procedure included four injections (ADP, oligomycin, FCCP, and rotenone). Baseline OCR and stimulated (with 400 µM ADP) OCR were measured and indicated as state 2 and state 3, respectively. Following ADP depletion, oligomycin (4 µM) was added. State 4 is the OCR after the addition of oligomycin, indicating the ATP-independent respiration. Carbonyl cyanide 4-(trifluoromethoxy) phenylhydrazone (FCCP, 2 µM) was added to measure maximal uncoupled respiration and rotenone (1 μM) was used to measure the proton leak. Calculated proton leak estimated by subtracting difference between oligomycin induced OCR from antimycin OCR measurements in Sham vs CA mitochondria.

Mouse Echocardiography

M-mode echocardiography was performed to monitor the cardiac function on the mice anesthetized with 3% vaporized isoflurane. Mice were secured to a Vevo 2100 (VisualSonics, Toronto, ON, Canada) platform and monitored for temperature, heart rate, and electrocardiogram as previously described (29). Transthoracic echocardiography was performed using a parasternal long-axis approach to obtain 2D left ventricular images. M-mode images were used to measure left ventricular end-diastolic and end-systolic size, and to calculate the percent fractional shortening (FS %).

Hematoxylin and Eosin (H&E) Staining

H&E staining was prepared by University of Chicago Human Tissue Research Center. Histopathological changes in paraffin embedded hearts were examined by doing whole slide scan.

CD31 Staining

Frozen sections (7 μm) of mouse heart were fixed in methanol, blocked with albumin (Sigma, St. Louis, MO), and incubated with primary antibodies CD31 and Dystrophin for 1 hour at 25° C. (mouse monoclonal anti-dystrophin, 1:1000 dilution, rabbit polyclonal anti-CD31, 1:500). Immunostaining was performed using standard procedures (32). Images were obtained with 31 Marianas Yokogawa-type spinning disk confocal system (Yokogawa, Tokyo, Japan) and capillary densities were analyzed by using ImageJ (NIH, Bethesda, MD).

Tetrazolium Staining

Tetrazolium staining on the mice hearts was described previously (33). The hearts were freshly taken and went through a freeze-thaw cycle by wrapping heart with a clean food wrap. They were kept at −20° C. for 1-2 h. Once the hearts were solid, they were cut into 3 mm slices. The slices were incubated in 1% tetrazolium salt solution stain at 37° C. for 15-20 min. The heart slices were then washed in PBS and the images were taken under natural light.

Terminal Deoxynucleotidyl Transferase Mediated Biotin Nick End-Labeling (TUNEL) Assay Myocardium apoptosis was assessed by using TACS 2-TdT Blue Apoptosis Detection Kit (Trevigen, Inc., MD) according to the manufacturer's instructions and as previously described (34). Briefly, frozen sections (7 μm) of mouse heart were fixed with 3.7% formaldehyde in PBS for 10 min and then incubated in proteinase K at room temperature for 20 min. The sections were incubated with labeling buffer for 5 min, followed by 60 min of incubation at 37° C. in labeling reaction mix containing dNTP, TdT enzyme, $CoCl_2$, and labeling buffer. The positive control was created by incubating the control slide in 1:50 TACS Nuclease buffer. The slides were then mounted with Prolong Gold antifade mounting medium (Life Technologies, Eugene, OR).

Mitochondrial ROS Measurement (MitoSox Staining)

ROS measurements were made as described previously (29). Briefly, the heart sections (10 μm) were cut on a cryostat, mounted on glass slides, and stored at −70° C. At time of mitochondrial ROS measurement, slides were thawed, washed in PBS, and stained with 5 μM MitoSox in the dark for 20 min. After staining, slides were washed in PBS and imaged immediately on a Zeiss fluorescent microscope. With the addition of 10 mM pyruvate+2 mM malate, Mitosox staining on isolated mitochondria was measured after 15 minutes incubation in 5 μM MitoSox in the dark for 20 minutes. The mitochondrial ROS production was quantified by measuring red fluorescence (485/530 nm) and analyzed by using ImageJ (NIH, Bethesda, MD).

Statistics

Comparisons between groups containing normally distributed data were made using ANOVA with Tukey's test or the Student t-test. Mann-Whitney test and Kruskal-Wallis test was applied for nonparametric statistics. The survival curves were compared using a Log Rank (Mantel Cox) test. Analysis was performed using Prism software (Graph Pad, La Jolla, CA, USA). Data were presented as mean±SEM. Values of $P<0.05$ were considered statistically significant.

Results

Cardiac Arrest Duration Determines Post-CPR Myocardial Dysfunction and Resuscitation Outcomes Using a previously established model of induced asystolic CA, the effects of cardiac duration on resuscitation outcomes were investigated (14). Baseline characteristics of the mice and CPR quality were recorded (Table 1).

TABLE 1

Pre cardiac arrest baseline characteristics of mice with 4-minutes, 8-minutes, 12-minutes, and 16-minutes of cardiac arrest.

| Parameters | Sham (n = 8) | CA4 (n = 8) | CA8 (n = 20) | CA12 (n = 20) | CA16 (n = 8) | P Value |
|---|---|---|---|---|---|---|
| Body weight (g) | 26.9 ± 0.52 | 27.0 ± 0.46 | 27.1 ± 0.27 | 27.4 ± 0.40 | 27.4 ± 0.40 | P > 0.05 |
| Heart Rate (bpm) | 532 ± 27.6 | 531 ± 27.9 | 535 ± 15.4 | 535 ± 16.1 | 529 ± 31.4 | P > 0.05 |
| CPR rate (bpm) | 350 ± 4.5 | 357.3 ± 4.0 | 347.2 ± 5.0 | 342.7 ± 6.8 | 355.5 ± 2.5 | P > 0.05 |

Values = means ± SE; n, number of animals.

Figures 1A, 1B, 1C, 1D, 1E, 1F:
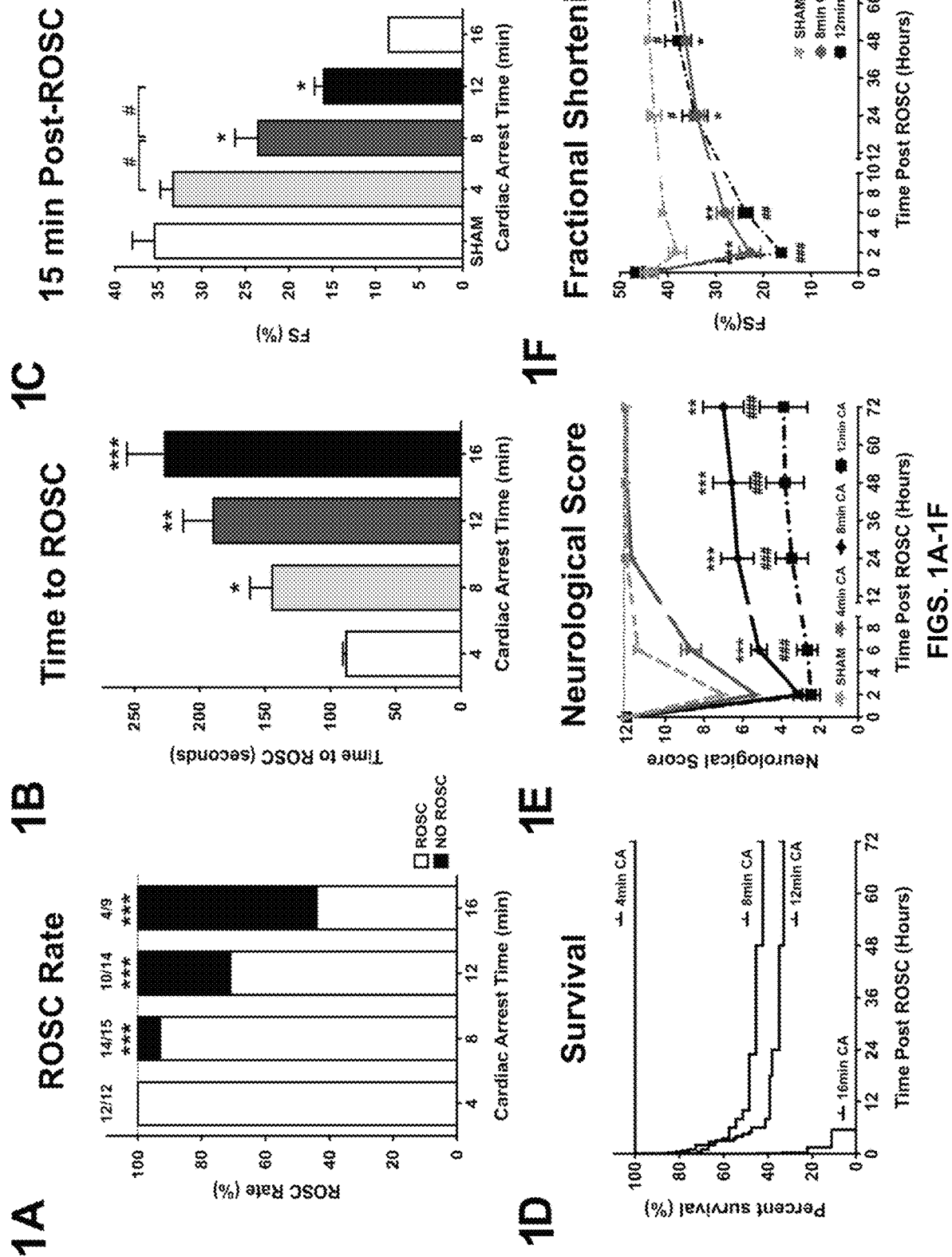
FIGS. 1A-1F: Duration of cardiac arrest determines post-CPR outcomes. 1(A) Return of spontaneous circulation rates (ROSC) following 4,8,12, and 16 minutes of CA. 1(B) Time of CPR to achieve ROSC. n=12, 15, 14, 9, respectively. *, $P<0.05$; , $P<0.01$; *, $P<0.001$ vs 4-minute group. 1(C) Percent left ventricular fractional shortening 15 minutes after achieving ROSC for different durations of CA. n=17, 12, 12, 12, 1, respectively. 1(D) Kaplan Meyer Curve demonstrating survival following different durations of CA. n=22, 28, 34, 9, respectively. 1(E) Neurological scores following CA of increasing duration. n=12, respectively. 1(F) Percent left ventricular fractional shortening recovery over time following CA. n=7, 7, 9, respectively. *, $P<0.05$; , $P<0.01$; *, $P<0.001$ vs Sham. #, $P<0.05$.

Increasing the duration of CA reduced rates of return to spontaneous circulation (ROSC) and increased the CPR time needed to achieve ROSC (ROSC rate: 100%, 93%, 71% and 44% in 4, 8, 12, and 16-minute groups, respectively; Time to ROSC: 88±2 minutes, 145±17 minutes, 189±23 minutes, and 227±29 minutes, respectively. FIGS. 1A and 1B). Post-CPR myocardial dysfunction was proportional to the duration of CA (Fractional shortening at 15 minutes post-ROSC: 35±2%, 33±1%, 24±3%, 16±1%, and 9% in Sham, 4, 8, 12, and 16-minute groups, respectively. FIG. 1C) and predicted survival 2 hours after ROSC (FIG. 1D). CA duration also correlated strongly with the severity of neurological injury over 72 hours after ROSC (FIG. 1E). Despite being severely depressed during the first 6 hours following ROSC, myocardial function gradually improved to near baseline measurements over the following 72 hours (Fractional shortening at 72 hours post-ROSC: 41±1% in Sham, 39±2% in 12-minute group, FIG. 1F). These data are consistent with clinical observations, which show that post-CPR outcomes worsen as a function of CA duration (2, 6) and that post-CPR myocardial dysfunction recovers over time (22).

Post-CPR Myocardial Dysfunction is Consistent with Myocardial Stunning

Figure 3A:
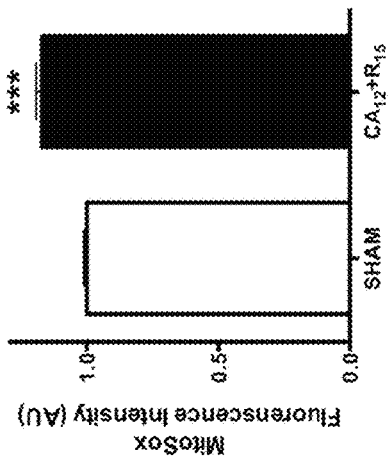
FIGS. 3A-3D: Increased ROS production and decreased complex I activity post CPR resuscitation. 3(A) Calcium induced mitochondrial swelling from Sham and post-CPR heart. n=2, 3, 3, 3, respectively. 3(B) MitoSox staining from CA and Sham mice heart. Fluorescence quantification is demonstrated in left graphic. n=4, respectively. 3(C) Fluorescence quantification of MitoSox staining on mitochondria isolated from CA and Sham mice with the present of 10 mM pyruvate+2 mM malate. n=4, respectively. 3(D) Complex I activity measurement directly from cardiac mitochondria. n=4, respectively. CA12+R15, 12-min CA+15-min resuscitation; *, $P<0.05$; ***, $P<0.001$ vs Sham.
Figure 3B:
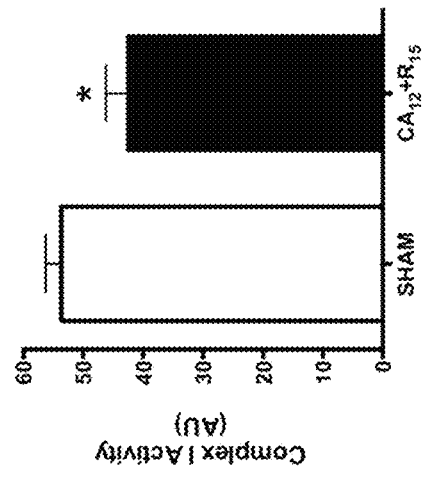
Figure 3C:
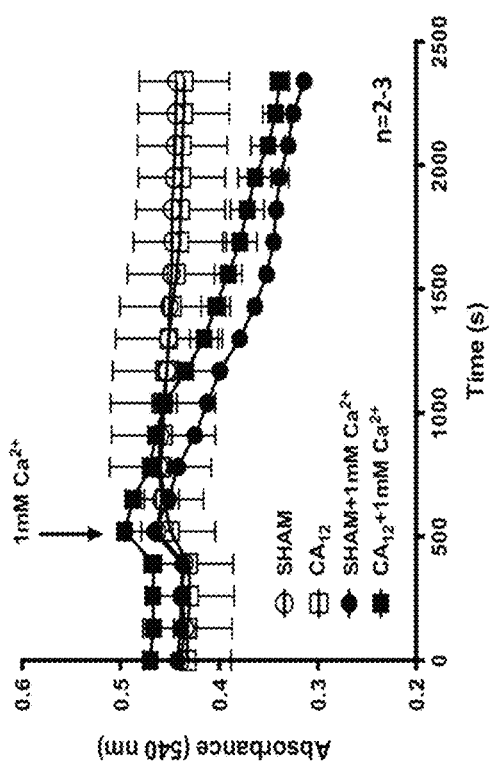
Figure 3D:
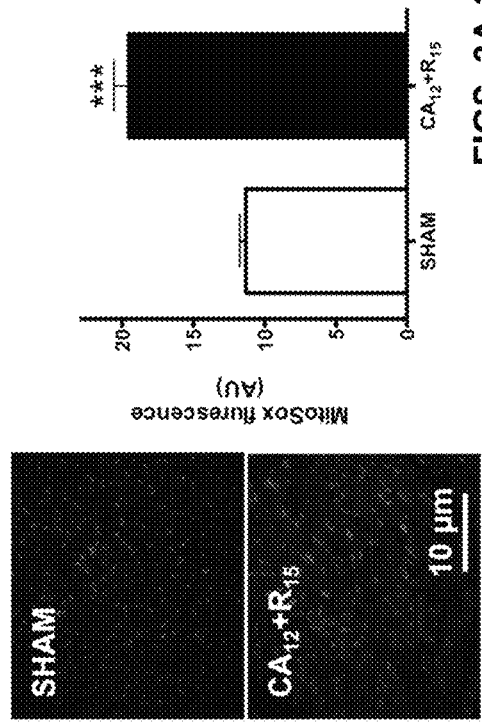

Next, it was determined whether post-CPR myocardial dysfunction was the result of cardiomyocyte cell death. Tetrazolium staining and histological examination revealed no evidence of myocardial necrosis (FIGS. 2A and 2B), while TUNEL staining and CD31 staining showed no evidence of cardiomyocyte apoptosis or endothelial cell loss (FIGS. 2C, 2D, and 7). Increased sensitivity to mitochondrial permeability transition pore opening (MPTP) which is associated with myocardial infarction was not observed in mitochondria isolated 15 min following ROSC compared to Shams (FIG. 3A). However, time dependent increases in reactive oxygen species (ROS) were measured in post-CA tissue (FIG. 3B) and mitochondria (FIG. 3C) compared to Shams (FIG. 8). In addition, complex I activity reduced in post-CA mitochondria compared to Shams (FIG. 3D). Together, these observations indicate that post-CA myocardial dysfunction is associated with post-CPR mitochondrial ROS and mitochondrial dysfunction.

Mitochondrial Injury and Complex I and II Function Following Successful CPR

Figures 4A, 4B, 4C, 4D, 4E:
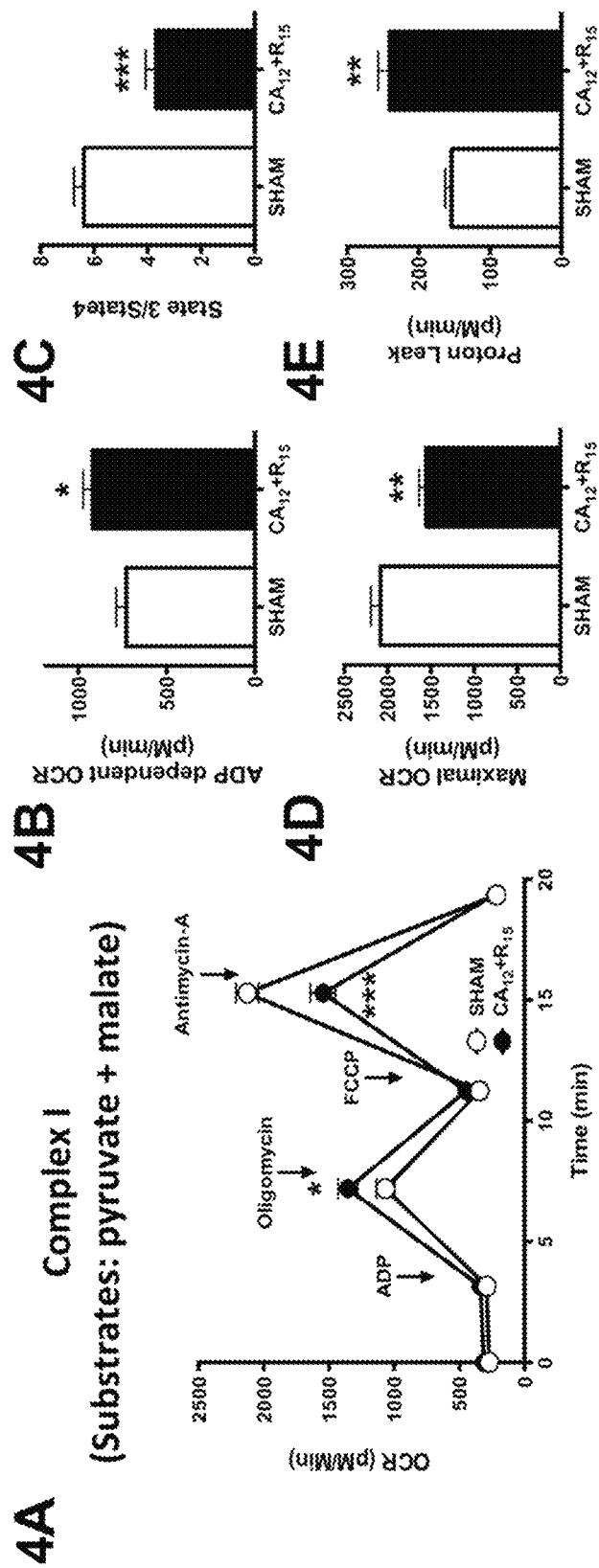
FIGS. 4A-4E: Post-CPR mitochondrial complex I injury. Oxygen consumption rate (OCR) measurements of cardiac mitochondria from CA and Sham. 4(A) The sequential injection of mitochondrial inhibitors is indicated by arrows. 4(B) ADP stimulated OCR. 4(C) State 3/State 4 respiration. 4(D) FCCP stimulated OCR. 4(E) Calculated proton leak. n=7, respectively. CA12+R15, 12-min CA+15-min resuscitation; *, $P<0.05$; , $P<0.01$; *, $P<0.001$ vs Sham.

Mitochondrial oxygen consumption was measured in isolated mitochondria from post-CA and Sham mice to further characterize post-CA mitochondrial dysfunction. Following the administration of adenosine diphosphate (ADP) to induce mitochondrial respiration, oxygen consumption rates (OCR) (FIGS. 4A and 4B) increased as expected in both post-CPR mitochondria and Sham mitochondria (919±55 vs. 729±57 µM/min). Paradoxically, these increases were greater in the damaged post-CPR mitochondria than in the Sham mitochondria but occurred in the context of increased mitochondrial proton leak (241±16 vs. 154±9 µM/min, FIG. 4E), suggesting that ADP stimulated increases in OCR were reflective of increased ROS production rather than that of ATP production. Further evidence of post-CPR mitochondria damage was the depressed OCR observed upon maximal OCR respiration stimulated by the uncoupler FCCP (1547±97 vs. 2127±86 µM/min in Sham, FIG. 4D) and decreases in mitochondrial efficiency of oxygen consumption based on state 3/state 4 ratios following CA compared to Sham (3.7±0.4 vs. 6.3±0.4, FIG. 4C). These results are consistent with the decreased Complex I activity measured directly from cardiac mitochondria after CA and further demonstrate the association of mitochondrial injury at Complex I following post-CA resuscitation (FIG. 3D).

Figures 9A, 9B, 9C, 9D, 9E:
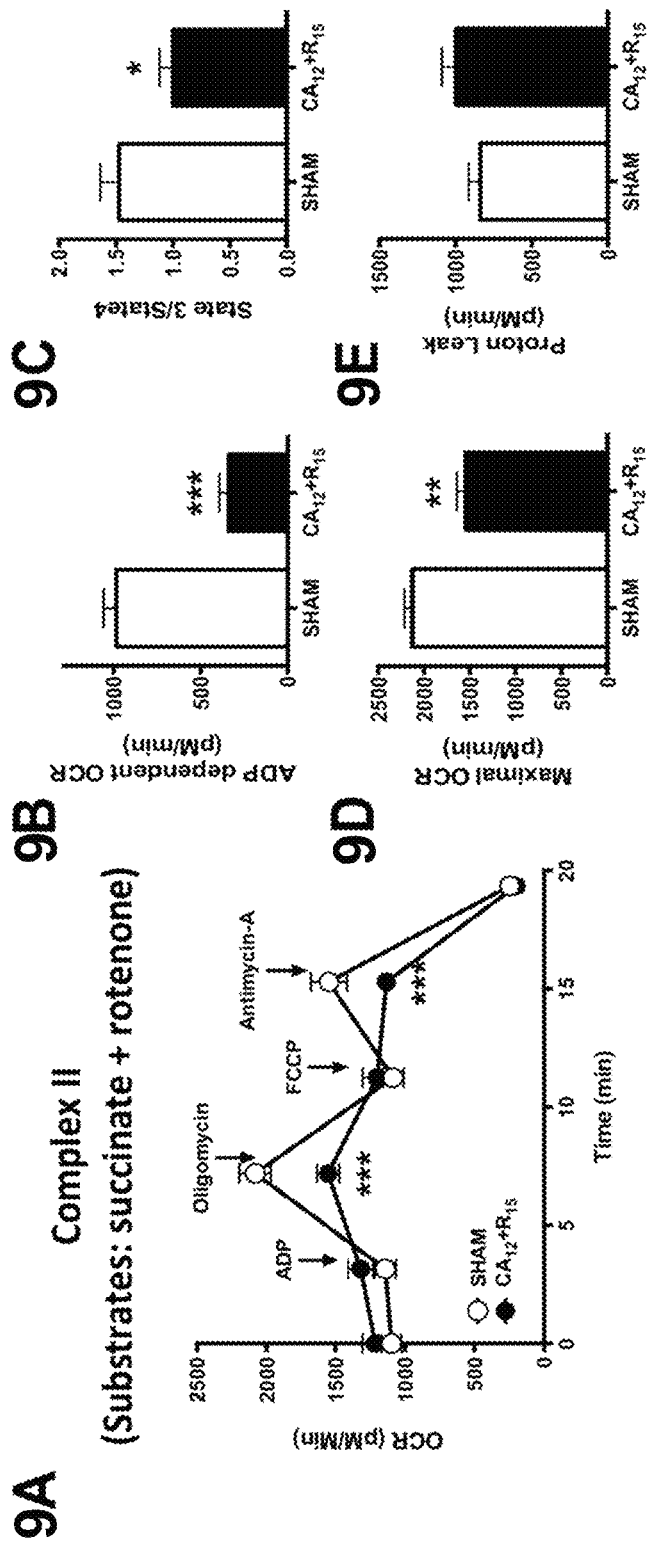

Similar to Complex I, experiments designed to measure OCR at Complex II found decreases OCR in post-CPR mitochondria stimulated by FCCP compared to Shams (1554±83 vs. 2082±115 µM/min, FIG. 9A). However, unlike Complex I, Complex II ADP dependent OCR decreased compared to Sham mitochondria (340±52 vs. 985±74 µM/min, FIG. 9B) with no significant differences in proton leak (998±93 vs. 838±76 µM/min, FIG. 4E). These experiments demonstrate that mitochondrial injury occurs following cardiac arrest resuscitation and that Complex I injury differs fundamentally from Complex II injury suggesting increased ROS production from this site.

Figures 5A, 5B, 5C, 5D, 5E, 5F:
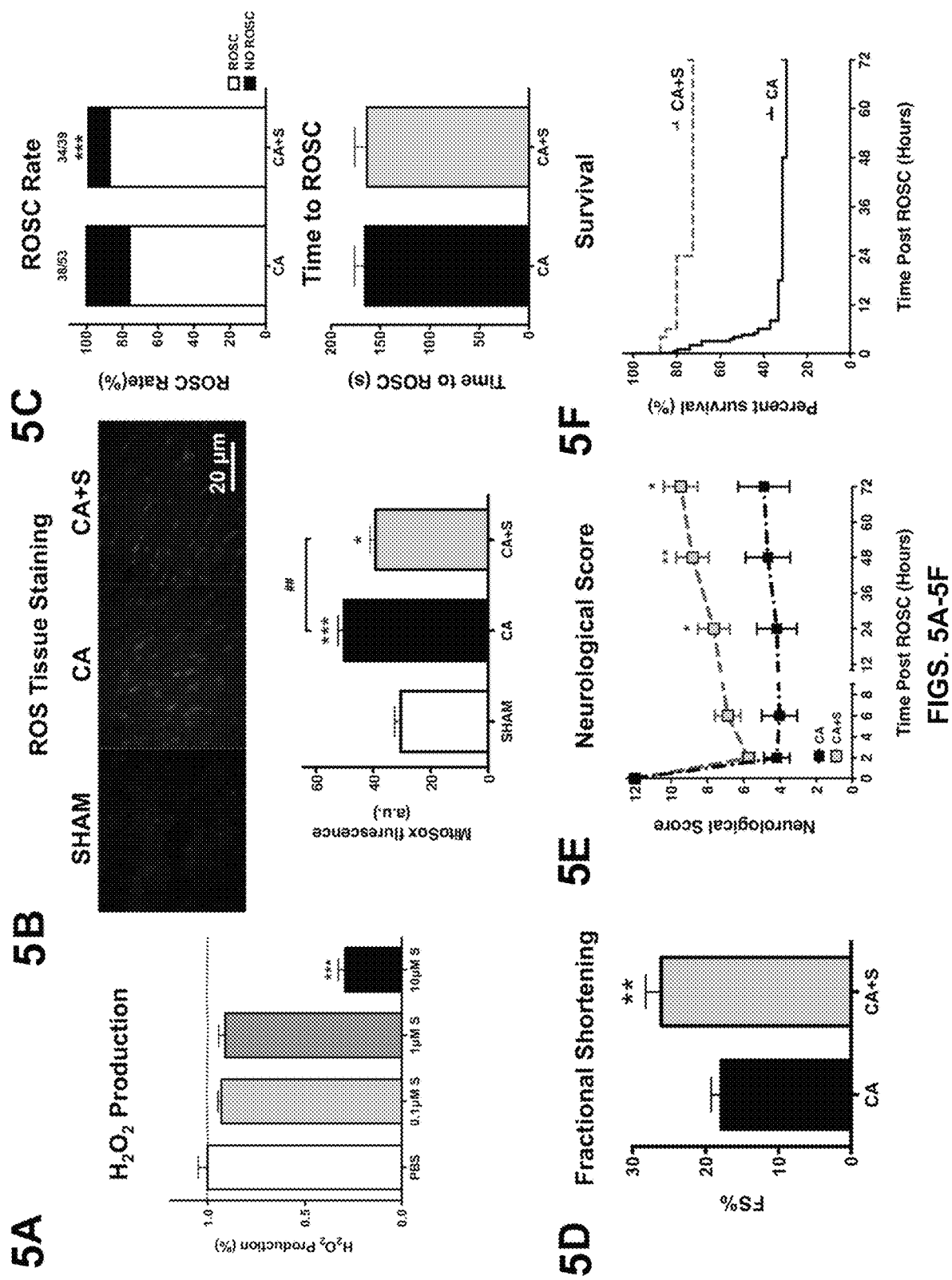
FIGS. 5A-5F: S1QEL reduces post-CPR myocardial stunning and improves post CPR resuscitation outcomes. 5(A) Effects of S1QEL (0.1 µM, 1 µM and 10 µM) on succinate-induced $H_2O_2$ production at site $I_Q$ of complex I post CA. n=16, 16, 22, 16, respectively. ***, $P<0.001$ vs CA group. 5(B) Images and bar graph show that MitoSox staining in the heart tissue following CPR with and without S1QEL. n=9, 10, 8, respectively. *, $P<0.05$; ***, $P<0.001$ vs Sham. ##, $P<0.01$ vs CA group. 5(C) ROSC following 12 minutes of CA and CPR time to ROSC with S1QEL and controls. n=53, 39, respectively. 5(D) Left ventricular fractional shortening following 12-min CA with S1QEL and controls. n=10, 8, respectively. 5(E) Neurological scores in mice following CA with S1QEL and controls. n=14, 17, respectively. 5(F)

Inhibition of Complex I-Specific Superoxide Generation Reduces Myocardial Stunning and Improves Post-CPR Survival Since the results were indicative of increased ROS production from Complex I following CA resuscitation, it was next investigated whether a site-specific Complex I superoxide inhibitor S1QEL would improve post CPR outcomes. In dose response trials, it was found that a 10 µM of S1QEL was sufficient to inhibit $H_2O_2$ production in isolated mitochondria induced by 5 mM succinate at site $I_Q$ (FIG. 5A). The effects of blinded, randomized administration of S1QEL or PBS at the initiation of CPR were next tested. Baseline animal characteristics and CPR quality were similar in both groups (Table 2).

TABLE 2

Pre cardiac arrest baseline characteristics of mice with and without the treatment of S1QEL.

| Parameters | CA12 (n = 40) | CA12 + S1QEL (n = 40) | P Value |
|---|---|---|---|
| Body weight (g) | 27.2 ± 0.29 | 27.1 ± 0.28 | P > 0.05 |
| Heart Rate (bpm) | 534 ± 10.9 | 540 ± 11.4 | P > 0.05 |
| CPR rate (bpm) | 346.4 ± 4.2 | 346.2 ± 4.1 | P > 0.05 |

Values are means ± SE; n, number of animals.

Ten microliters of S1QEL reduced ROS production 15 minutes post CA (FIG. 5B) and increased the ROSC rate without altering the CPR time to ROSC (FIG. 5C). S1QEL was associated with improved post-CPR myocardial contractility, neurological function, and overall survival (fraction shortening at 2 h post-CPR: 26±2% vs. 18±1%; neurological score at 72 h post CPR: 9.5±1.0 vs. 4.9±1.4; survival rate at 72 h post CPR: 74% vs 30%. FIGS. 5D, 5E, and 5F). The beneficial effects of S1QEL occurred in a dose-dependent manner (FIG. 11) although S1QEL did not improve the outcomes following prolonged CA (16 minutes CA). (FIG. 12).

DISCUSSION

In this study, three key findings were made. First, post-CPR myocardial dysfunction following asystolic CA is due to myocardial stunning rather than myocardial necrosis (FIGS. 1A-2D). Although myocardial stunning is typically associated with ventricular wall movement abnormalities following brief coronary occlusion/reperfusion, this study demonstrates that stunning can occur in the context of global cardiac ischemia-reperfusion (IR) injury, which is experienced by patients resuscitated from CA. Myocardial dysfunction following induced asystolic CA has been described previously (14, 18), but in this study, it has been demonstrate for the first time in an asystolic CA model that post-CPR myocardial dysfunction is dependent on the length of arrest, not associated with myocardial necrosis/apoptosis, and is reversible; consistent with myocardial stunning. This stunning is similar to that previously reported in the setting of ventricular fibrillation in other animal models (8, 11). Findings of myocardial stunning described in this study and others are also consistent with reports of early recovery of myocardial function in survivors following CA in several clinical studies (23, 24).

Importantly, this study demonstrates the severity of myocardial stunning is determined by the length of CA, which is related to ROSC rates and survival. Stunning is thus a key determinant of early post-CPR mortality and is clinically relevant. Understanding the pathophysiology of stunning is of great translational relevance in the setting of post-CA resuscitation.

Second, it was discovered that post-CPR myocardial stunning occurs in the context of mitochondrial injury at Complexes I and II, resulting in a paradoxical increase in oxygen consumption at ETC Complex I (FIGS. 4A-4E and 9A-9E). As expected, the reduced maximal OCR at Complexes I and II and the decreased Complex I activity were observed, supporting the finding of Complex I injury following CA (FIG. 3D). Mitochondrial injury following post-CA resuscitation has been reported previously (25), but the unexpected observations reported here of increased OCR with ADP administration and increased proton leak at Complex I suggest that Complex I could be the site of increased ROS in post-CPR ventricular tissue and mitochondria. These observations are consistent with prior reports of Complex I injury associated with increased oxygen consumption and ROS generation after prolonged cardiac ischemia-reperfusion (18, 26, 27). The ROS generated following CPR in this study was not sufficient to generate opening of the mPTP, but could be responsible for the observed post-CPR myocardial dysfunction given that superoxide has been demonstrated to reduce myocardial filament contractile activity in vitro in a dose responsive manner (28).

Third, it was determined that S1QEL, a site $I_Q$-specific $H_2O_2$ production suppressor, limited ROS generation and neurological injury while improving ROSC rate, myocardial function, and survival following CA (FIGS. 5A-5F and 11A-11B). It is well known that myocardial IR injury increases ROS generation and that targeting Complex I-mediated ROS generation during reperfusion has therapeutic utility (9, 17, 18). However, a major limitation of these approaches is that they not only reduce ROS production but also limit electron flow through the ETC thus disrupting normal mitochondrial function to a significant degree. The findings of Brand M D et al. have shown S1QEL overcomes these limitations and have shown protective effects against oxidative damage, ER stress, and IR injury in the isolated perfused heart in a Langendorff preparation (16). It is not believed that S1QEL has not been studied previously in vivo in mammals. Here, it has been demonstrated that S1QEL improves post-CPR mitochondria function resulting in reduced ROS generation and improved cardiac, neurological, and survival outcomes in a mouse cardiac arrest model. Importantly, this work has translational significance because S1QEL was administered at the time of CPR initiation and limited the effects of reperfusion injury following CA. Future research into agents that can be administered to patients by paramedics in the field to limit post-CPR reperfusion injury could represent a major advance in the caring of post-CA patients.

Limitations: This study has several limitations. First, the study was performed in a murine model of asystolic CA. Although this model has several advantages including the ability to perform survival outcome studies and cost, the findings on the efficacy of S1QEL on myocardial function could benefit from study in other models of CA. Second, this study was not designed to determine the mechanism of S1QEL's neuroprotective effects. It is possible that S1QEL could have had direct effects on brain ischemia-reperfusion injury, although it is unknown if it is able to cross blood brain barrier. Additional experiments will be needed to address the effects of S1QEL specifically on post-CPR neurological injury.

Summary

In conclusion, post-CPR cardiogenic shock reflects ischemia/reperfusion induced myocardial stunning, the severity of which depends upon the length of cardiac standstill prior to CPR. This stunning can occur following asystolic CA or following arrhythmogenic induced CA (8, 11). Myocardial stunning is associated with a pattern of mitochondrial injury indicative of increased mitochondrial ROS generation at Complex I. Targeting mitochondrial Complex I ROS in the setting of post-CPR with specific inhibitors of electron leak (e.g., S1QEL) represents a novel, practical strategy to improve post-CPR resuscitation outcomes.

Various aspects of the disclosure are further exemplified by the non-limiting embodiments recited in the claims below. In each case, features of multiple claims can be combined in any fashion not inconsistent with the specification and not logically inconsistent.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

REFERENCES

1. Benjamin E J, Virani S S, Callaway C W, et al: Heart Disease and Stroke Statistics-2018 Update: A Report From the American Heart Association. *Circulation* 2018, 137(12):e67-e492.
2. Larsen M P, Eisenberg M S, Cummins R O, et al: Predicting survival from out-of-hospital cardiac arrest: a graphic model. *Ann Emerg Med* 1993, 22(11):1652-1658.
3. Kleinman M E, Brennan E E, Goldberger Z D, et al: Part 5: Adult Basic Life Support and Cardiopulmonary Resuscitation Quality: 2015 American Heart Association Guidelines Update for Cardiopulmonary Resuscitation and Emergency Cardiovascular Care. *Circulation* 2015, 132(18 Suppl 2):S414-435.
4. Babini G, Grassi L, Russo I, Novelli D, et al: Duration of Untreated Cardiac Arrest and Clinical Relevance of Animal Experiments: The Relationship Between the "No-Flow" Duration and the Severity of Post-Cardiac Arrest Syndrome in a Porcine Model. *Shock* 2018, 49(2):205-212.
5. Roberts B W, Kilgannon J H, Chansky M E, et al: Multiple organ dysfunction after return of spontaneous circulation in postcardiac arrest syndrome. *Crit Care Med* 2013, 41(6): 1492-1501.
6. Nolan J P, Neumar R W, Adrie C, et al: Post-cardiac arrest syndrome: epidemiology, pathophysiology, treatment, and prognostication. A Scientific Statement from the International Liaison Committee on Resuscitation; the American Heart Association Emergency Cardiovascular Care Committee; the Council on Cardiovascular Surgery and Anesthesia; the Council on Cardiopulmonary, Perioperative, and Critical Care; the Council on Clinical Cardiology; the Council on Stroke. *Resuscitation* 2008, 79(3):350-379.
7. Braunwald E, Kloner R A: The stunned myocardium: prolonged, postischemic ventricular dysfunction. *Circulation* 1982, 66(6):1146-1149.
8. Kern K B, Hilwig R W, Rhee K H, et al: Myocardial dysfunction after resuscitation from cardiac arrest: an example of global myocardial stunning. *J Am Coll Cardiol* 1996, 28(1):232-240.
9. Bolli R: Mechanism of myocardial "stunning". *Circulation* 1990, 82(3):723-738.
10. Hirschl R B, Heiss K F, Bartlett R H: Severe myocardial dysfunction during extracorporeal membrane oxygenation. *J Pediatr Surg* 1992, 27(1):48-53.
11. Yang L, Li C, Gao C, et al: Investigation of myocardial stunning after cardiopulmonary resuscitation in pigs. *Biomed Environ Sci* 2011, 24(2):155-162.
12. Abel E D: Mitochondrial dynamics and metabolic regulation in cardiac and skeletal muscle. *Trans Am Clin Climatol Assoc* 2018, 129:266-278.
13. Song M, Mihara K, Chen Y, S et al: Mitochondrial fission and fusion factors reciprocally orchestrate mitophagic culling in mouse hearts and cultured fibroblasts. *Cell Metab* 2015, 21(2):273-286.
14. Sharp W W, Beiser D G, Fang Y H, et al: Inhibition of the mitochondrial fission protein dynamin related protein 1 improves survival in a murine cardiac arrest model. *Crit Care Med* 2015, 43(2):e38-47.
15. Chouchani E T, Pell V R, Gaude E, et al: Ischaemic accumulation of succinate controls reperfusion injury through mitochondrial ROS. *Nature* 2014, 515(7527): 431-435.
16. Brand M D, Goncalves R L, Orr A L, et al: Suppressors of superoxide-$H_2O_2$ production at site IQ of mitochondrial complex I protect against stem cell hyperplasia and ischemia-reperfusion injury. *Cell Metab* 2016, 24(4):582-592.
17. Vanden Hoek T L, Shao Z, Li C, Zak R, Schumacker P T, Becker L B: Reperfusion injury on cardiac myocytes after simulated ischemia. *Am J Physiol* 1996, 270(4 Pt 2):H1334-1341.
18. Dezfulian C, Shiva S, Alekseyenko A, et al: Nitrite therapy after cardiac arrest reduces reactive oxygen species generation, improves cardiac and neurological function, and enhances survival via reversible inhibition of mitochondrial complex I. *Circulation* 2009, 120(10):897-905.
19. Chouchani E T, Methner C, Nadtochiy S M, et al: Cardioprotection by S-nitrosation of a cysteine switch on mitochondrial complex I. *Nat Med* 2013, 19(6):753-759.
20. Zhao D, Abella B S, Beiser D G, et al: Intra-arrest cooling with delayed reperfusion yields higher survival than earlier normothermic resuscitation in a mouse model of cardiac arrest. *Resuscitation* 2008, 77(2):242-249.
21. Piao L, Sidhu V K, Fang Y H, et al: FOXO1-mediated upregulation of pyruvate dehydrogenase kinase-4 (PDK4) decreases glucose oxidation and impairs right ventricular function in pulmonary hypertension: therapeutic benefits of dichloroacetate. *J Mol Med* (Berl) 2013, 91(3):333-346.
22. Jentzer J C, Anavekar N S, Mankad S V, et al: Changes in left ventricular systolic and diastolic function on serial echocardiography after out-of-hospital cardiac arrest. *Resuscitation* 2018, 126:1-6.
23. Laurent I, Monchi M, Chiche J D, et al: Reversible myocardial dysfunction in survivors of out-of-hospital cardiac arrest. *J Am Coll Cardiol* 2002, 40(12):2110-2116.
24. Chang W T, Ma M H, Chien K L, et al: Postresuscitation myocardial dysfunction: correlated factors and prognostic implications. *Intensive Care Med* 2007, 33(1):88-95.
25. Dezfulian C, Kenny E, Lamade A, et al: Mechanistic characterization of nitrite-mediated neuroprotection after experimental cardiac arrest. *J Neurochem* 2016, 139(3): 419-431.
26. Gorenkova N, Robinson E, Grieve D J, et al: Conformational change of mitochondrial complex I increases ROS sensitivity during ischemia. *Antioxid Redox Signal* 2013, 19(13):1459-1468.
27. Paradies G, Petrosillo G, Pistolese M, et al: Decrease in mitochondrial complex I activity in ischemic/reperfused rat heart: involvement of reactive oxygen species and cardiolipin. *Circ Res* 2004, 94(1):53-59.
28. MacFarlane N G, Miller D J: Depression of peak force without altering calcium sensitivity by the superoxide anion in chemically skinned cardiac muscle of rat. *Circ Res* 1992, 70(6):1217-1224.
29. Sharp W W, Beiser D G, Fang Y H, et al: Inhibition of the mitochondrial fission protein dynamin-related protein 1 improves survival in a murine cardiac arrest model. *Crit Care Med* 2015, 43(2):e38-47.
30. Abella B S, Zhao D, Alvarado J et al. Intra-arrest cooling improves outcomes in a murine cardiac arrest model. Circulation. 2004, 109(22):2786-91.
31. Brand M D, Goncalves R L, Orr A L, et al: Suppressors of superoxide-$H_2O_2$ production at site $I_Q$ of mitochondrial complex I protect against stem cell hyperplasia and ischemia-reperfusion injury. *Cell Metab* 2016, 24(4):582-592.
32. Zhao D, Abella B S, Beiser D G, et al: Intra-arrest cooling with delayed reperfusion yields higher survival than earlier normothermic resuscitation in a mouse model of cardiac arrest. *Resuscitation* 2008, 77(2):242-249.
33. Ytrehus K, Liu Y, Tsuchida A, et al: Rat and rabbit heart infarction: effects of anesthesia, perfusate, risk zone, and method of infarct sizing. *Am J Physiol* 1994, 267(6 Pt 2):H2383-2390.
34. Sharp W W, Fang Y H, Han M, et al: Dynamin-related protein 1 (Drp1)-mediated diastolic dysfunction in myocardial ischemia-reperfusion injury: therapeutic benefits of Drp1 inhibition to reduce mitochondrial fission. *FASEB J* 2014, 28(1):316-326.
35. Song M, Mihara K, Chen Y, S et al: Mitochondrial fission and fusion factors reciprocally orchestrate mitophagic culling in mouse hearts and cultured fibroblasts. *Cell Metab* 2015, 21(2):273-286.

What is claimed is:

1. A method of treating or preventing post-cardiopulmonary resuscitation (CPR) injury following a cardiac arrest in a subject, comprising:
   administering a pharmaceutical composition to the subject, the pharmaceutical composition comprising a therapeutically effective amount of SIQEL,
   wherein the post-CPR injury is myocardial stunning,
   wherein the cardiac arrest is an asystolic cardiac arrest,
   and wherein the cardiac arrest lasts under 16 minutes.

2. The method of claim 1, wherein the pharmaceutical composition improves post-CPR mitochondrial function in the subject.

3. The method of claim 1, wherein the pharmaceutical composition reduces post-CPR cardiac mitochondrial ROS generation in the subject.

4. The method of claim 1, wherein the pharmaceutical composition increases the rate of post-CPR return to spontaneous circulation in the subject.

5. The method of claim 1, wherein the pharmaceutical composition increases post-CPR myocardial contractility in the subject.

6. The method of claim 1, wherein the pharmaceutical composition improves post-CPR neurological function in the subject.

7. The method of claim 1, wherein the pharmaceutical composition reduces post-CPR neurological injury in the subject.

8. The method of claim 1, wherein the pharmaceutical composition improves survival rate in the subject.

9. The method of claim 1, wherein the pharmaceutical composition is administered to the subject prior to, at the same time as, and/or after administration of cardiopulmonary resuscitation to the subject.

10. The method of claim 1, wherein the pharmaceutical composition further comprises one or more secondary therapeutic agents.

11. The method of claim 10, wherein the one or more secondary therapeutic agents is selected from adrenaline (epinephrine), atropine, amiodarone, adenosine, calcium chloride, chlorphenamine, furosemide, glucose, hydrocortisone, lidocaine, magnesium sulfate, midazolam, naloxone, sodium chloride, potassium chloride, and sodium bicarbonate, and mixtures thereof.

12. The method of claim 1 further comprising administering a therapeutically effective amount of a secondary therapeutic agent to the subject prior to, at the same time as, and/or after administration of the pharmaceutical composition to the subject.

13. The method of claim 12, wherein the one or more secondary therapeutic agents is selected from adrenaline (epinephrine), atropine, amiodarone, adenosine, calcium chloride, chlorphenamine, furosemide, glucose, hydrocortisone, lidocaine, magnesium sulfate, midazolam, naloxone, sodium chloride, potassium chloride, and sodium bicarbonate, and mixtures thereof.

14. A device for treating a subject in need of CPR following a cardiac arrest, comprising: a therapeutically effective amount of SIQEL; and further comprising a pre-filled syringe, an ampoule, an autoinjector, a nasal insufflator, a metered-dose inhaler, a dry-powder inhaler, a vaporizer, a nebulizer, a pump sprayer, an aerosol can, a softgel, or a dermal patch, wherein the treatment prevents post-CPR injury in the subject, wherein the post-CPR injury is myocardial stunning, wherein the cardiac arrest is an asystolic cardiac arrest, and wherein the cardiac arrest lasts under 16 minutes.

15. A pharmaceutical composition, comprising:
  a therapeutically effective amount of SIQEL;
  a pharmaceutically acceptable carrier, solvent, adjuvant, diluent, or a combination thereof; and
  one or more secondary therapeutic agents, wherein the pharmaceutical composition is used to treat or prevent post-CPR injury following a cardiac arrest, wherein the post-CPR injury is myocardial stunning, wherein the cardiac arrest is an asystolic cardiac arrest, and wherein the cardiac arrest lasts under 16 minutes.

16. The pharmaceutical composition of claim 15, wherein the one or more secondary therapeutic agents is selected from adrenaline (epinephrine), atropine, amiodarone, adenosine, calcium chloride, chlorphenamine, furosemide, glucose, hydrocortisone, lidocaine, magnesium sulfate, midazolam, naloxone, sodium chloride, potassium chloride, and sodium bicarbonate, and mixtures thereof.

* * * * *